(12) United States Patent
Thum et al.

(10) Patent No.: US 6,558,929 B2
(45) Date of Patent: May 6, 2003

(54) PCR REACTION MIXTURE FOR FLUORESCENCE-BASED GENE EXPRESSION AND GENE MUTATION ANALYSES

(75) Inventors: Thomas Thum, Hannover (DE); Jürgen Borlak, Lehrte OT Immensen (DE)

(73) Assignee: Fraunhofer-Gesellschaft zur Forderung der angewandten Forshung e.V., Munich (DE)

( * ) Notice: Subject to any disclaimer, the term of this patent is extended or adjusted under 35 U.S.C. 154(b) by 0 days.

(21) Appl. No.: 09/753,887

(22) Filed: Jan. 3, 2001

(65) Prior Publication Data

US 2002/0058255 A1 May 16, 2002

(30) Foreign Application Priority Data

Sep. 15, 2000 (DE) .......................................... 100 46 079

(51) Int. Cl.[7] .............................. C12Q 1/68; C12P 19/34
(52) U.S. Cl. ........................ 435/91.1; 435/6; 435/91.2
(58) Field of Search ........................... 435/6, 91.1, 91.2

(56) References Cited

U.S. PATENT DOCUMENTS

| | | | | |
|---|---|---|---|---|
| 5,759,822 A | * | 6/1998 | Chenchik et al. | 435/91.2 |
| 6,087,097 A | * | 7/2000 | Persing | 435/6 |
| 6,174,670 B1 | * | 1/2001 | Wittwer et al. | 435/6 |
| 6,395,547 B1 | * | 5/2002 | Stemmer et al. | 435/440 |

OTHER PUBLICATIONS

Kubalakova et al. "Optimization of PRINS and C–PRINS for detection of telomeric sequences in Vicia Faba" Biologica Plantarium 41 (2) 177–184, 1998.*

* cited by examiner

Primary Examiner—Jezia Riley
(74) Attorney, Agent, or Firm—Norris McLaughlin & Marcus

(57) ABSTRACT

An increase in the selectivity, sensitivity and the suppression of primer dimer formations, fluorescence-based gene expression analyses and gene mutation analyses is accomplished by adding bovine serum albumin to the conventional PCR reaction components. Magnesium chloride concentration is adjusted accurately depending on the Taq polymerase used.

22 Claims, 26 Drawing Sheets

Fluorescence Resonance Energy Transfer (FRET)

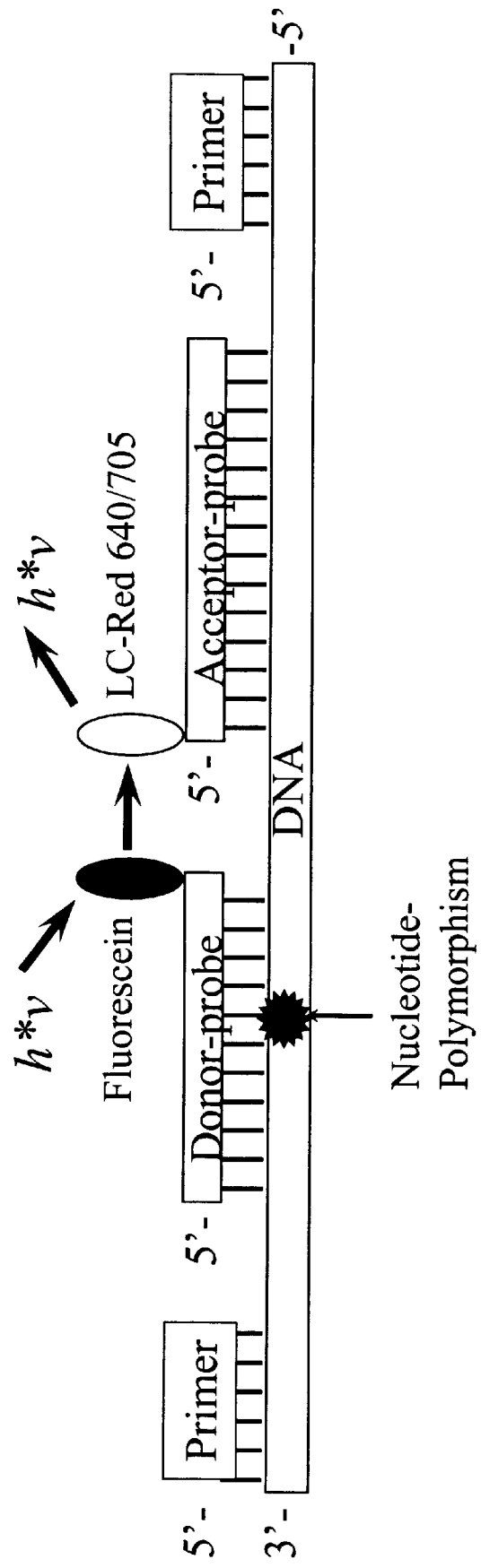
Fig. 1 Fluorescence Resonance Energy Transfer (FRET)

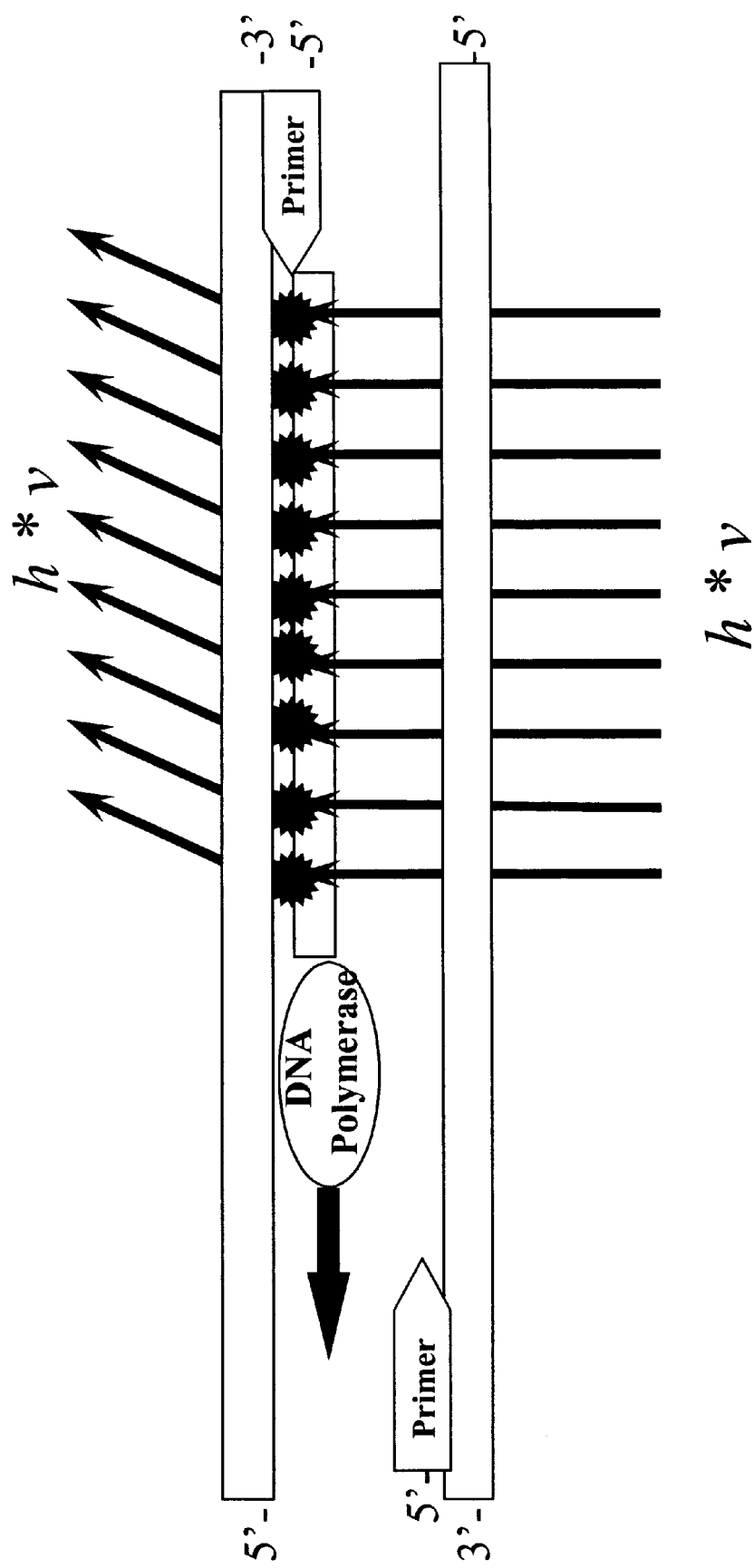
Fig. 2 SYBR-Green (✹) Labeling

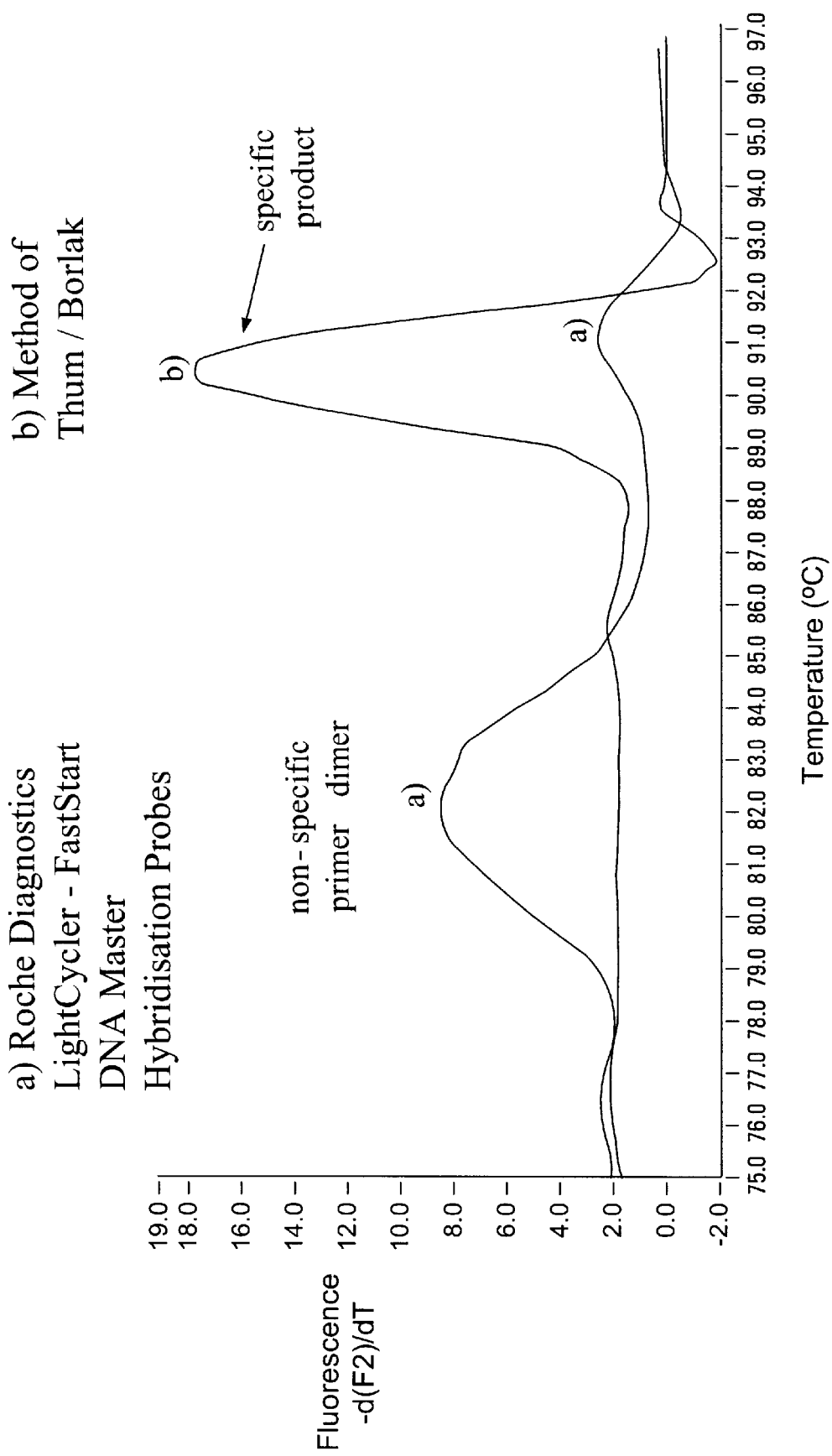

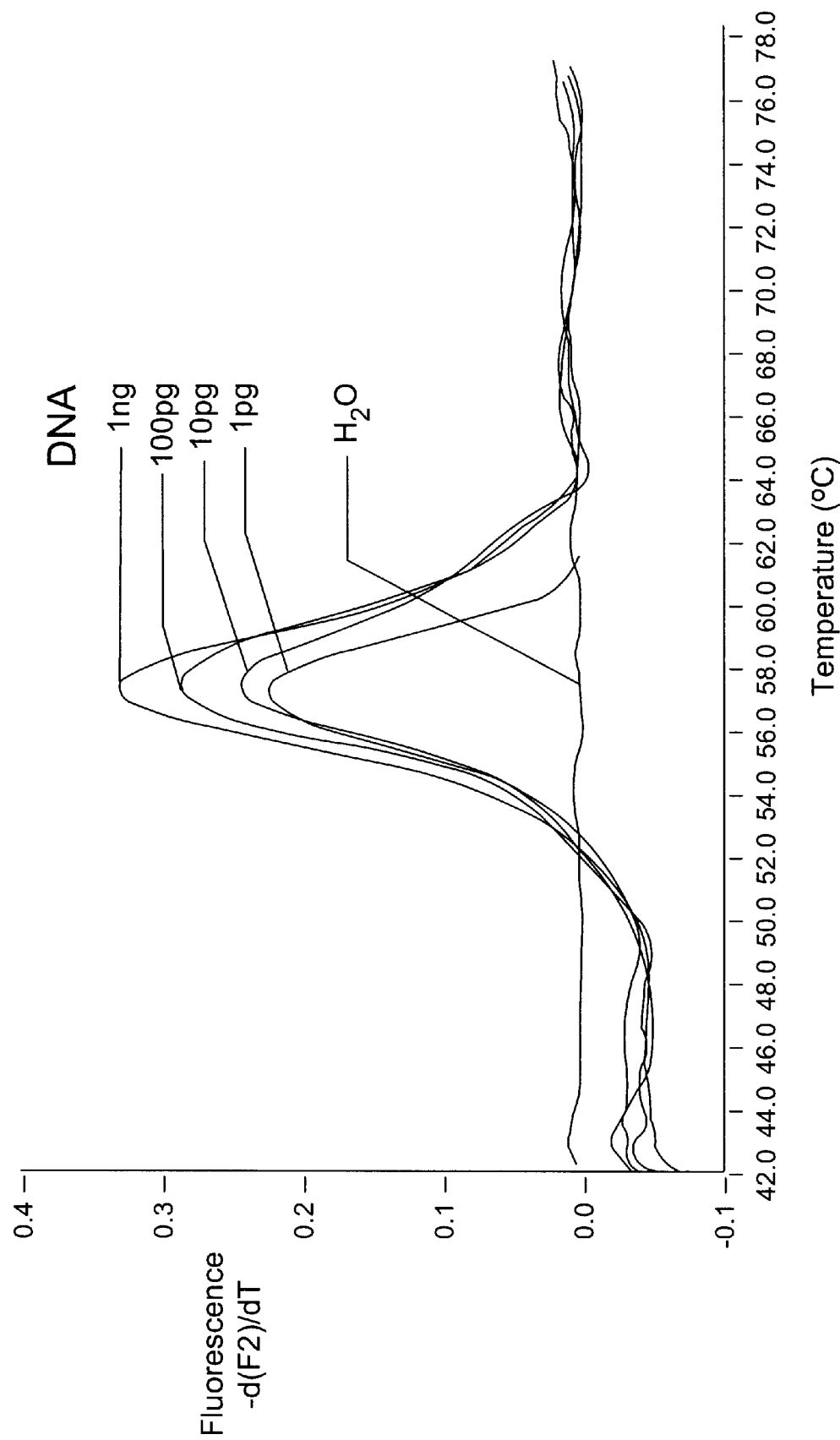
Fig. 4a: Method of Thum / Borlak

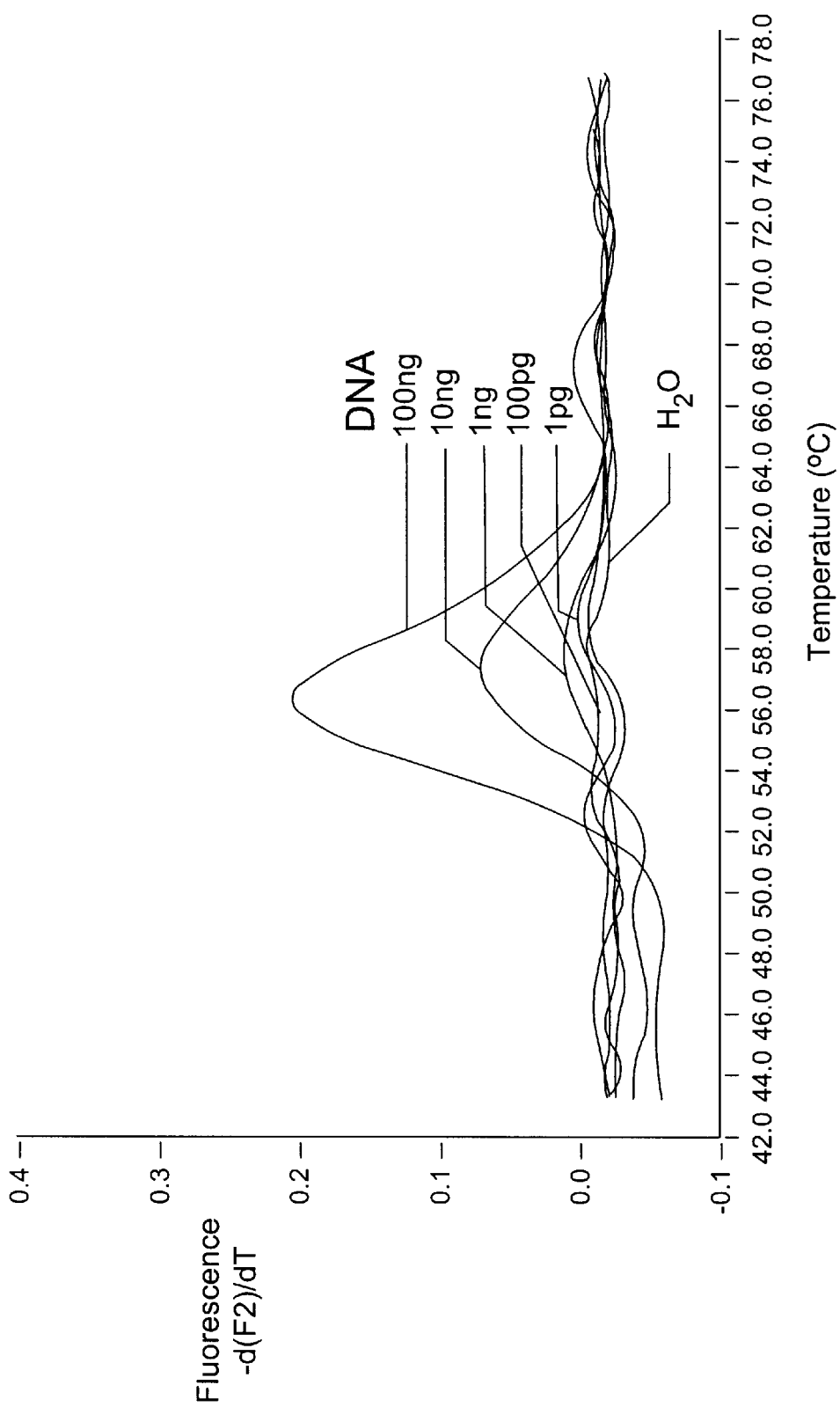
Fig. 4b: Roche Diagnostics LightCycler - FastStart DNA Master Hybridisation Probes

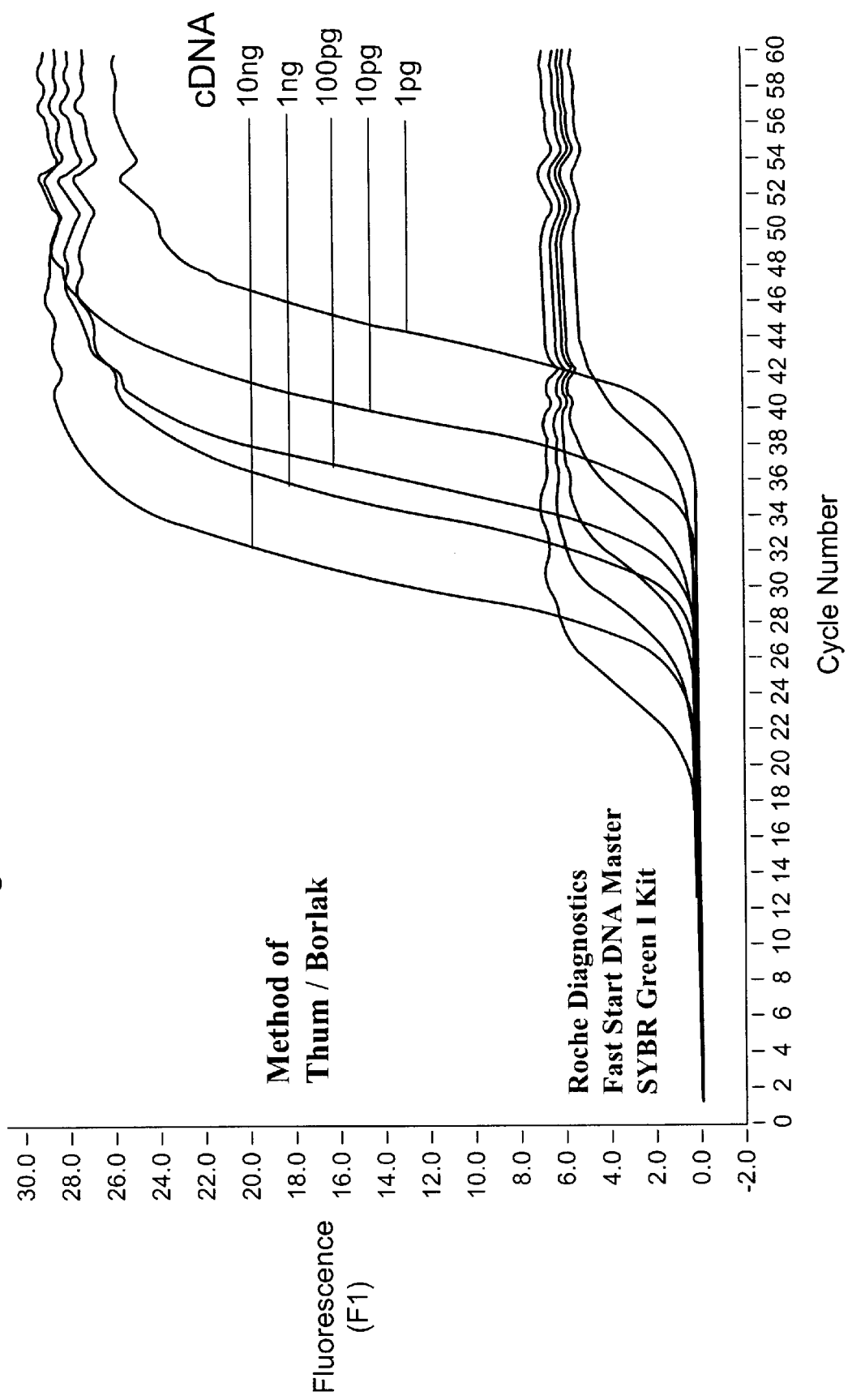
Fig. 5a: Amplification analysis

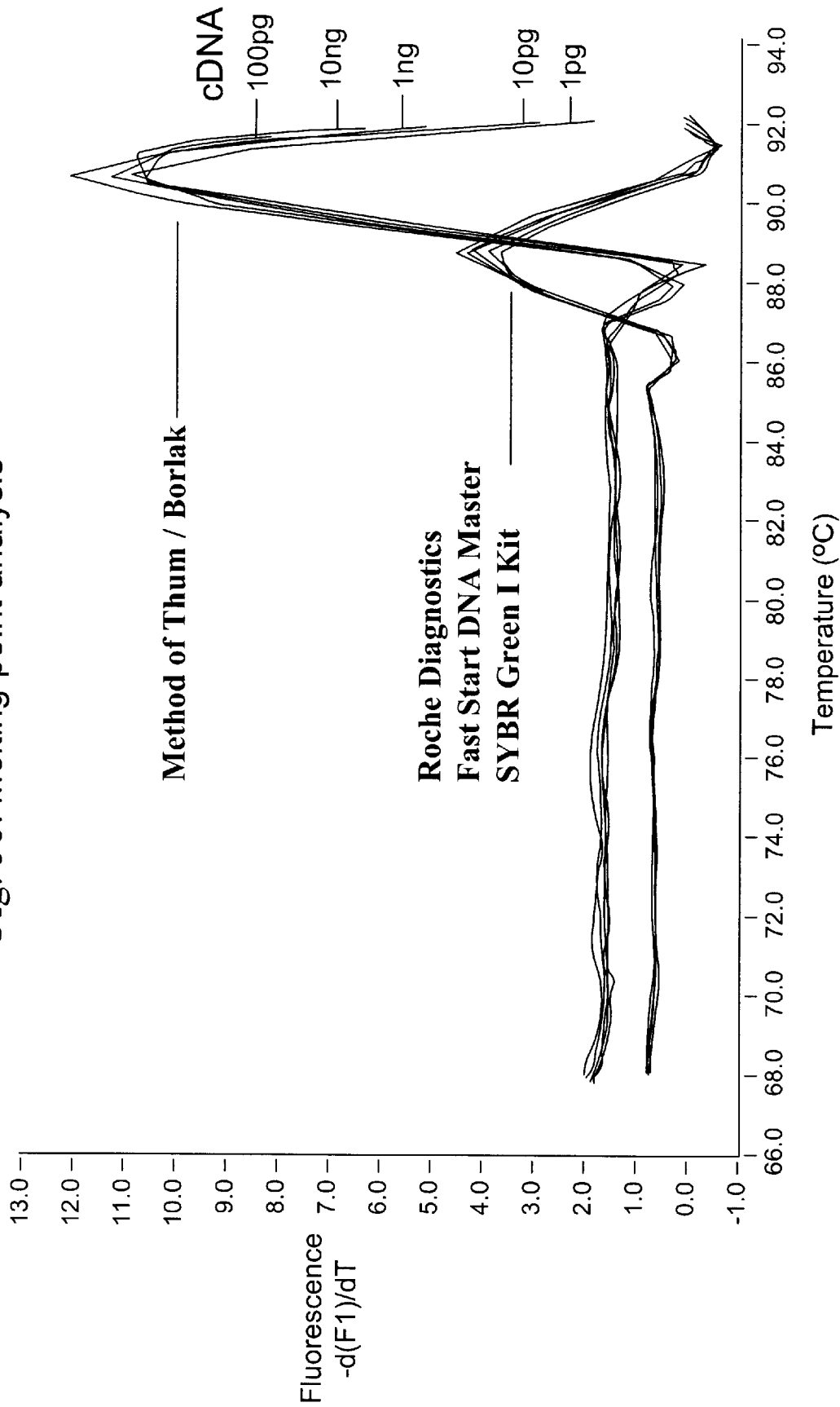
Fig. 5b: Melting point analysis

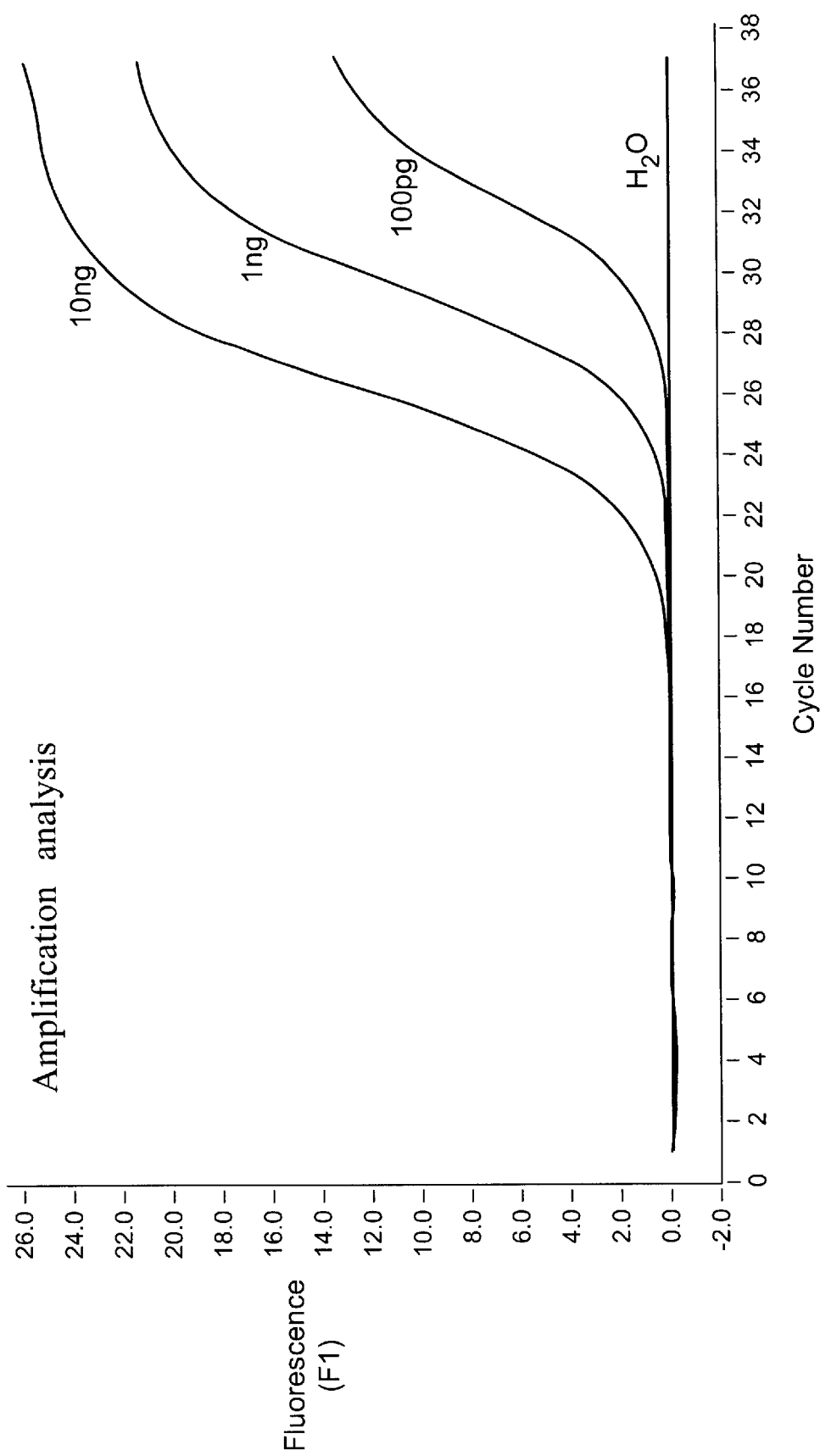

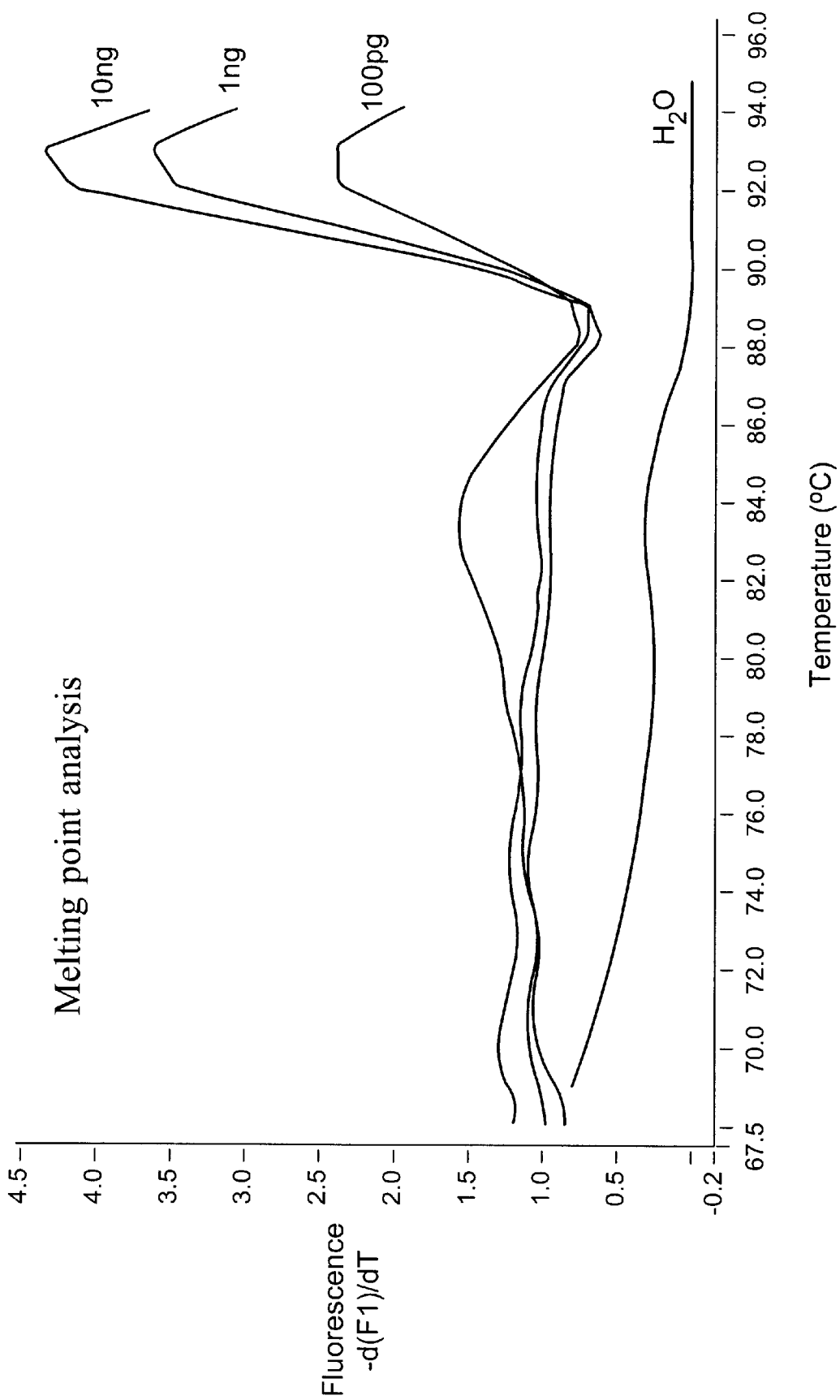
Fig. 6b: Detection of the beta-MHC-gene in the human heart

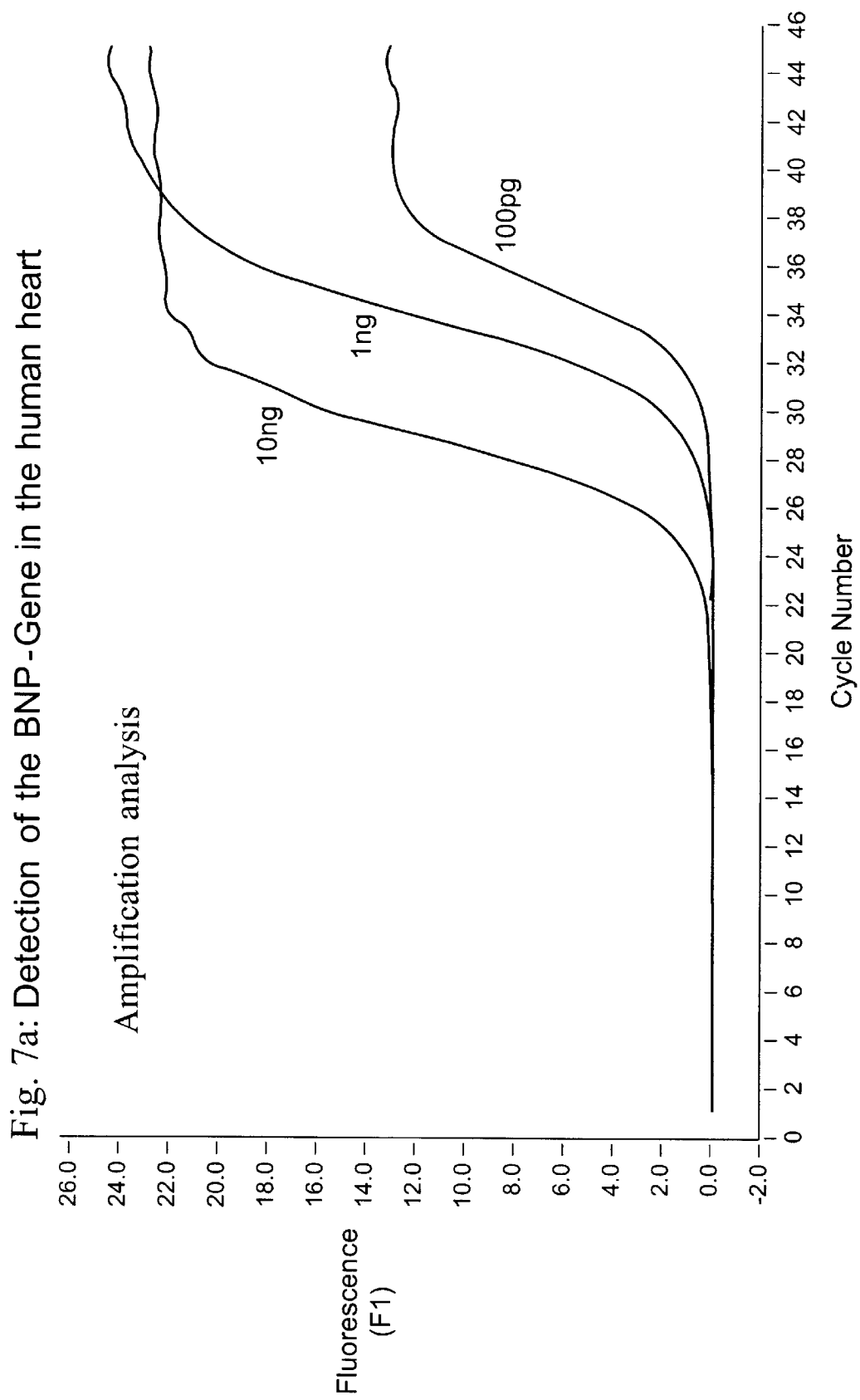

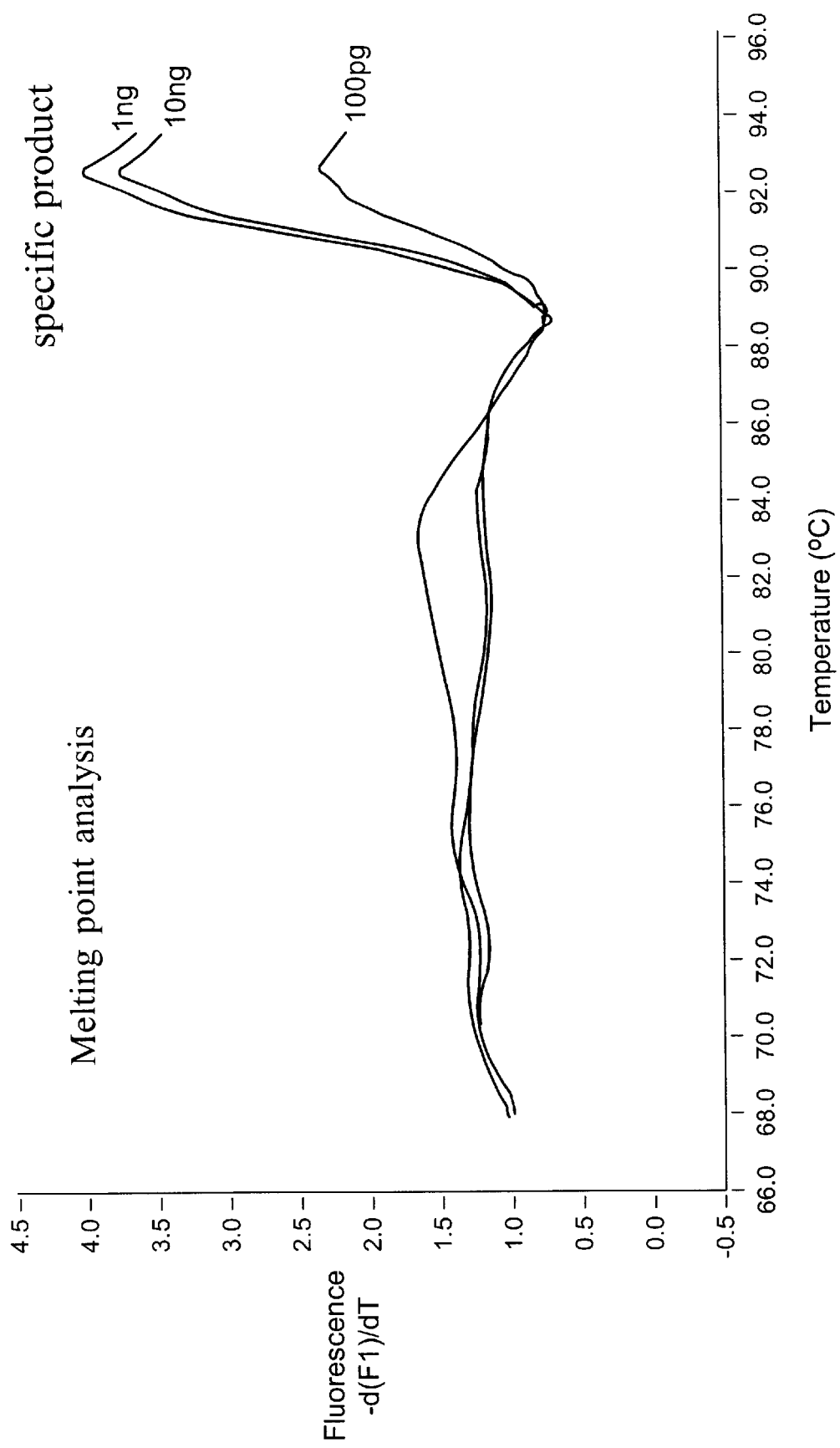
Fig. 7b: Detection of the BNP-Gene in the human heart

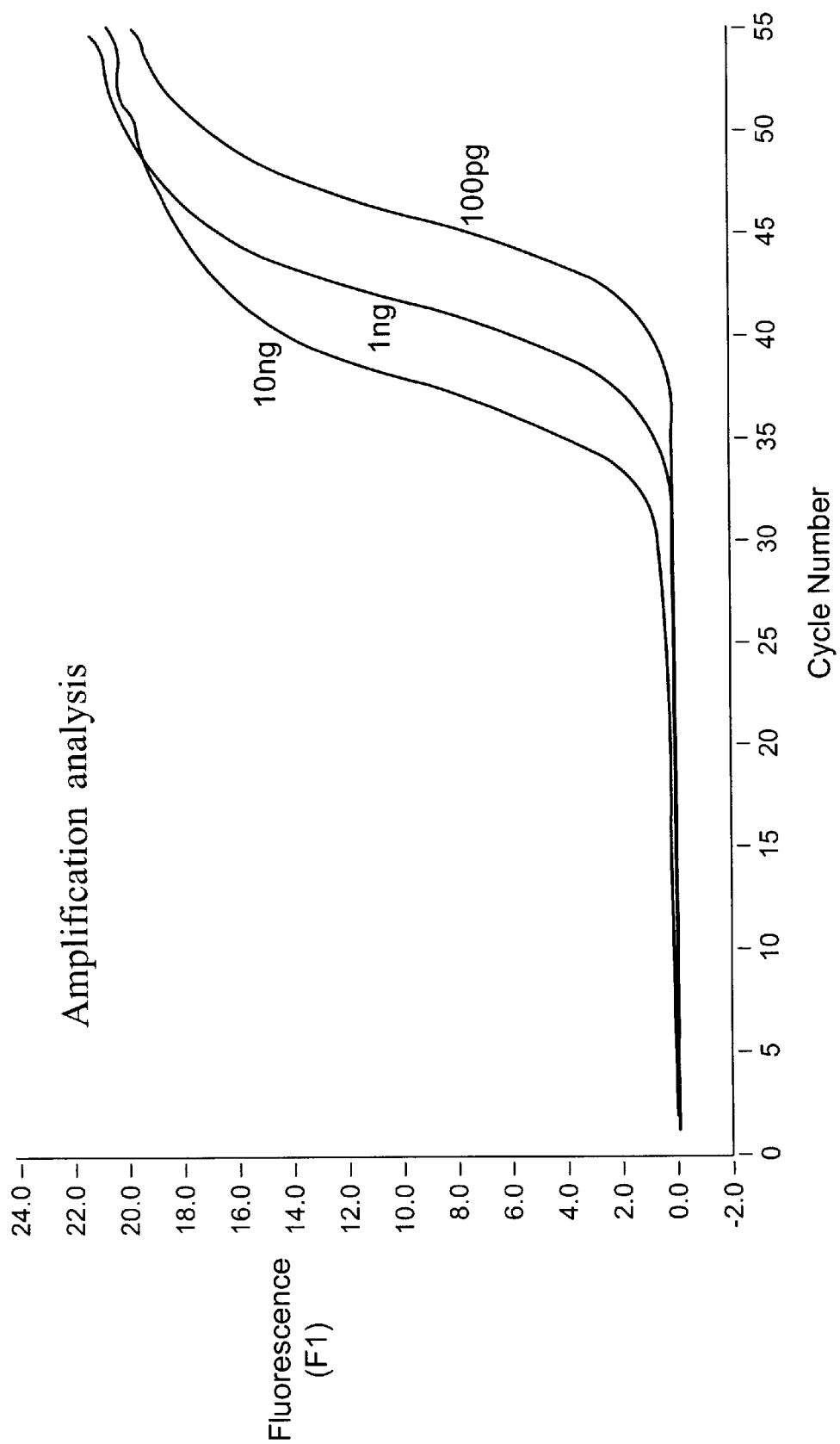
Fig.8a: Detection of the ANP-gene in cultured cardiomyocytes of the rat

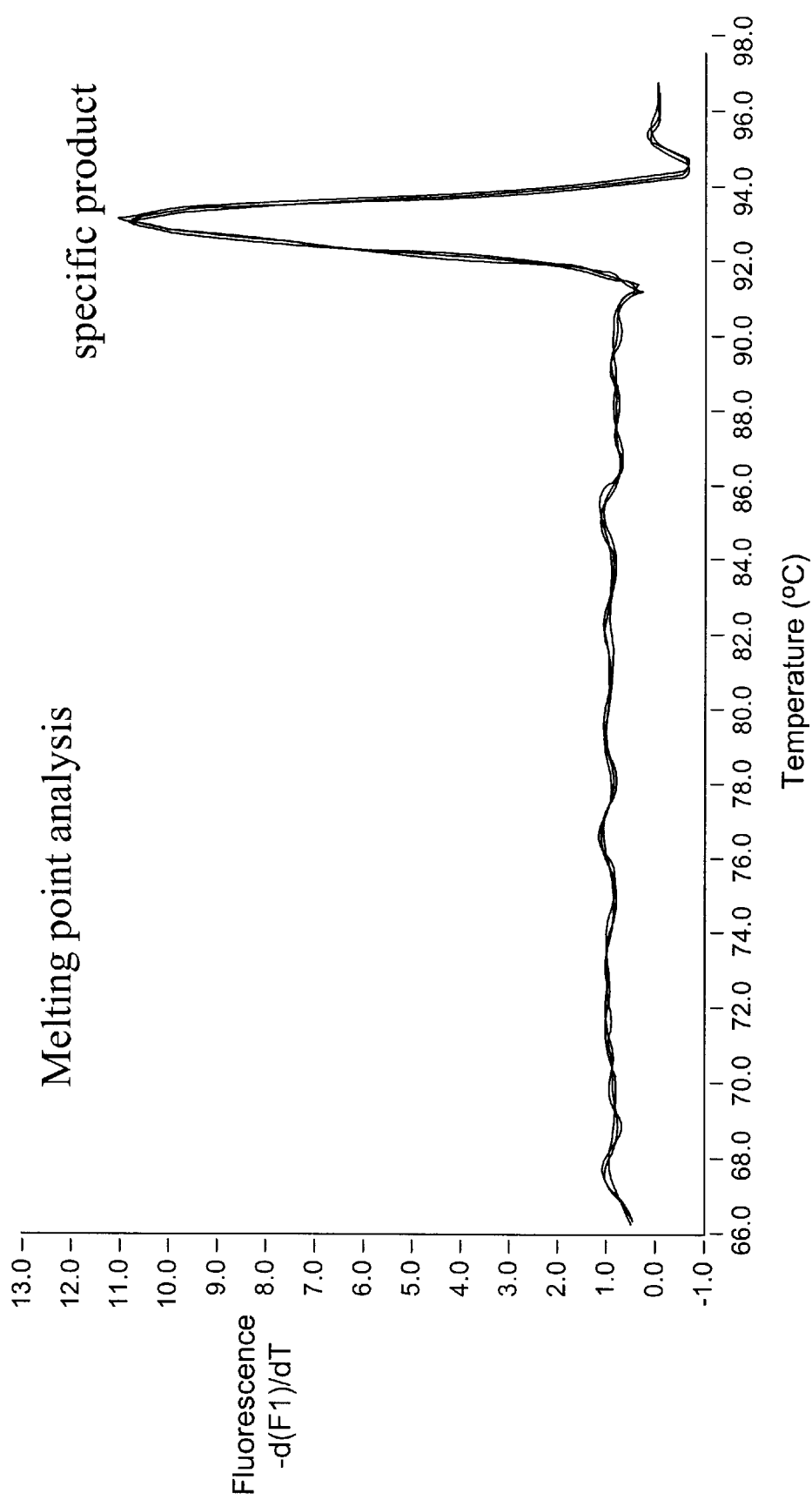
Fig. 8b: Detection of the ANP-gene in cultured cardiomyocytes of the rat

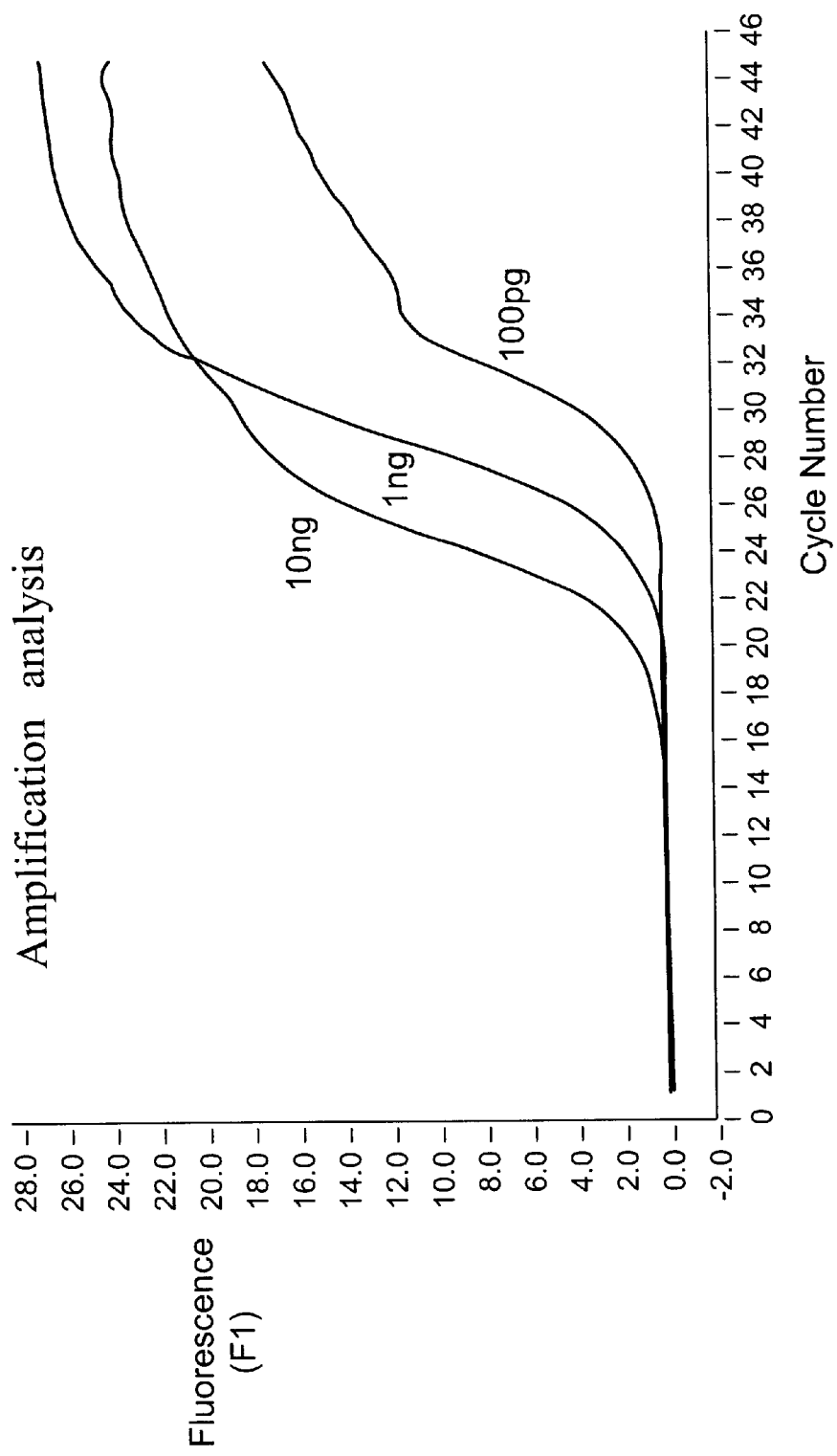
Fig.9a: Detection of the alpha skeleton Actin gene in heart tissue of the rat

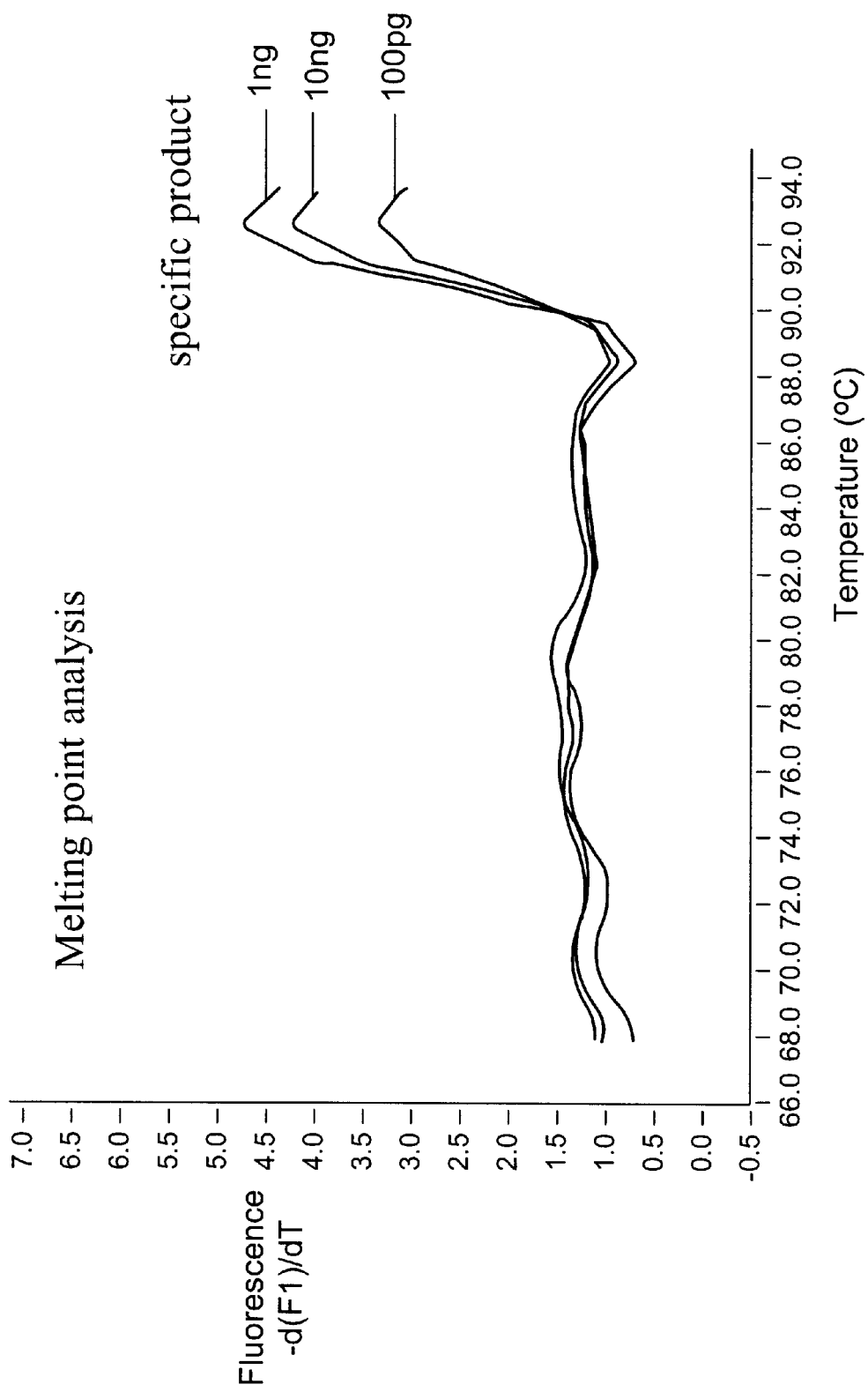
Fig.9b: Detection of the alpha skeleton Actin gene in heart tissue of the rat

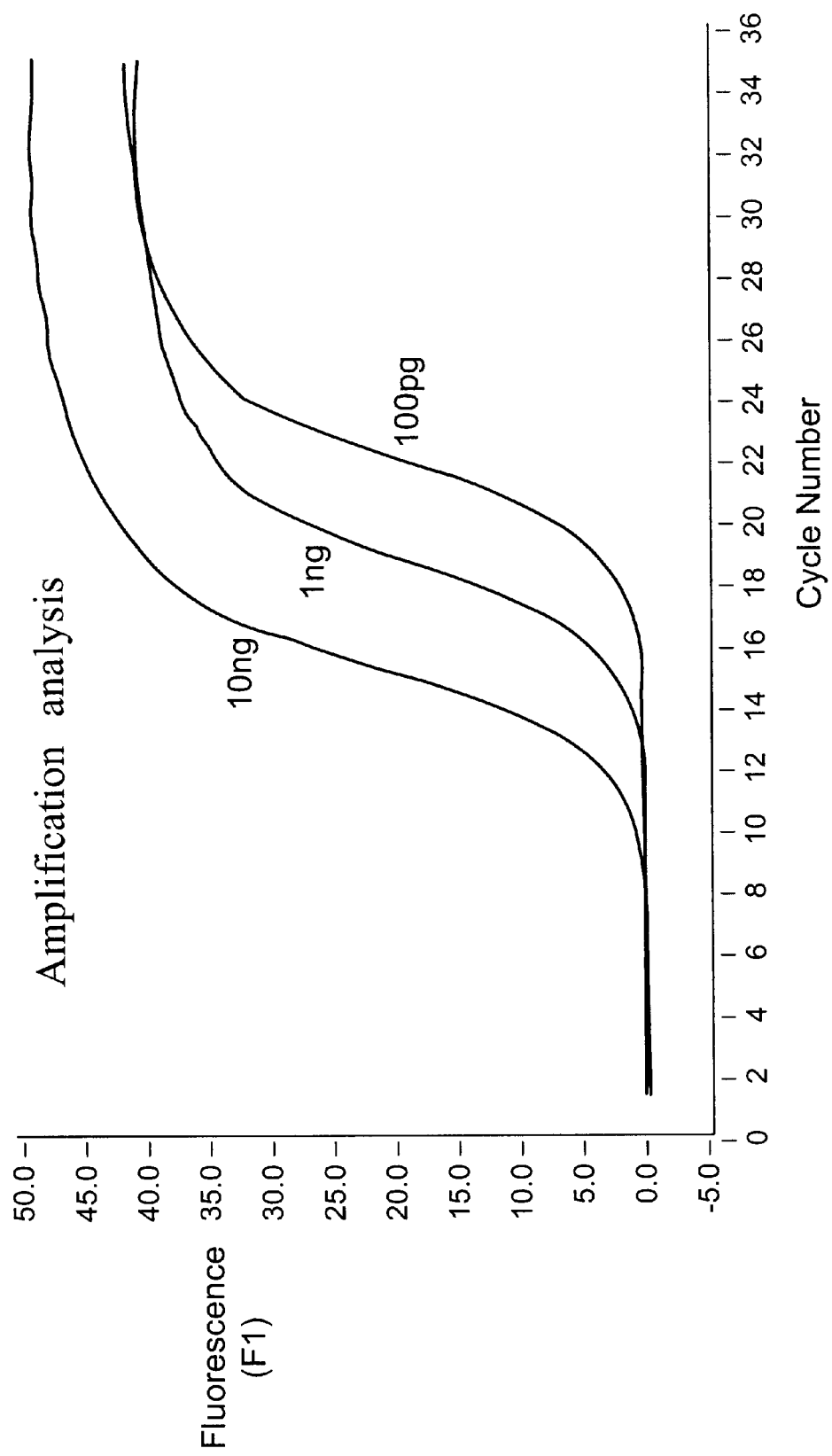
Fig. 10a: Detection of the Albumin gene in cultured hepatocytes of the rat

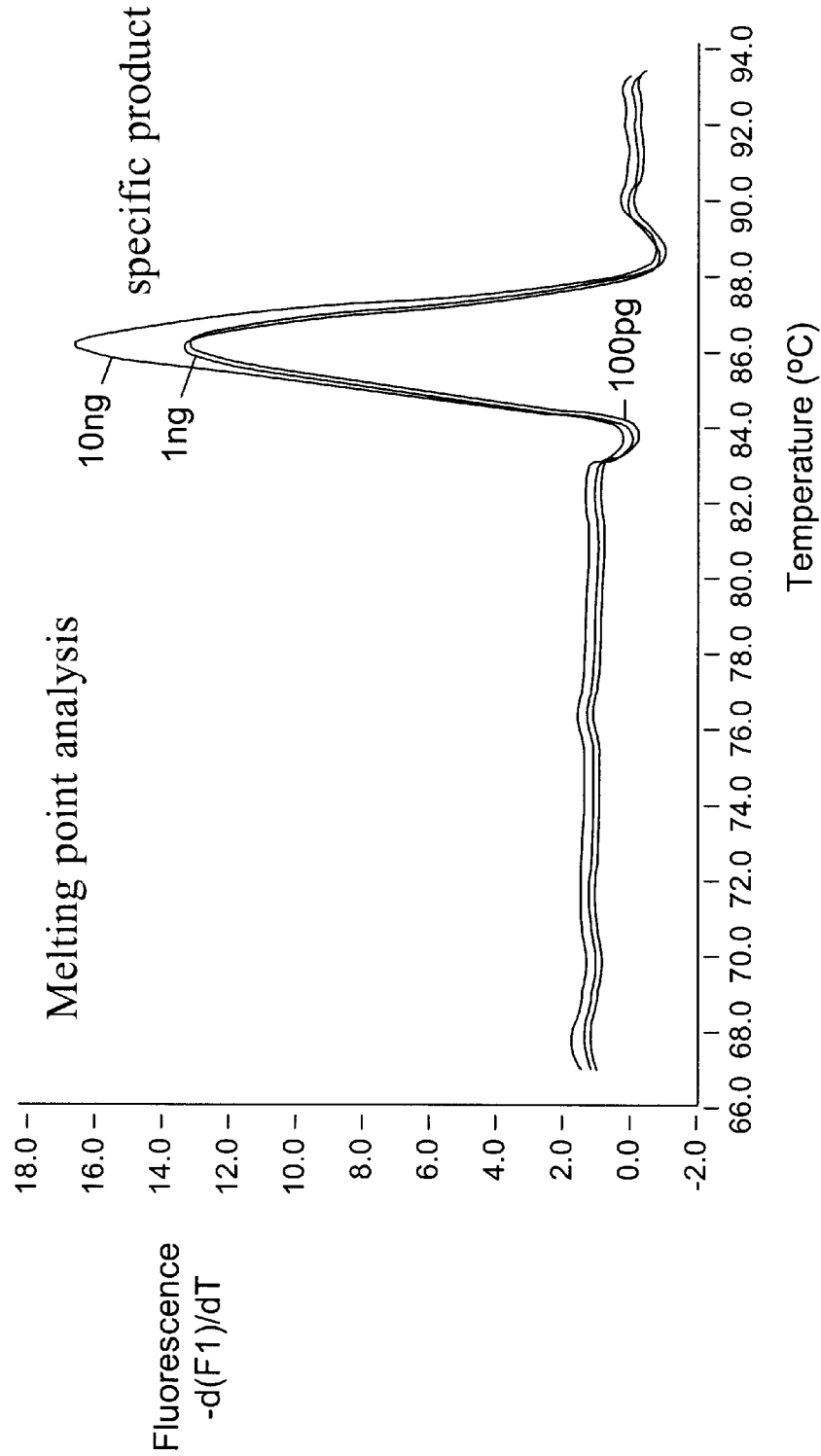
Fig. 10b: Detection of the Albumin gene in cultured hepatocytes of the rat

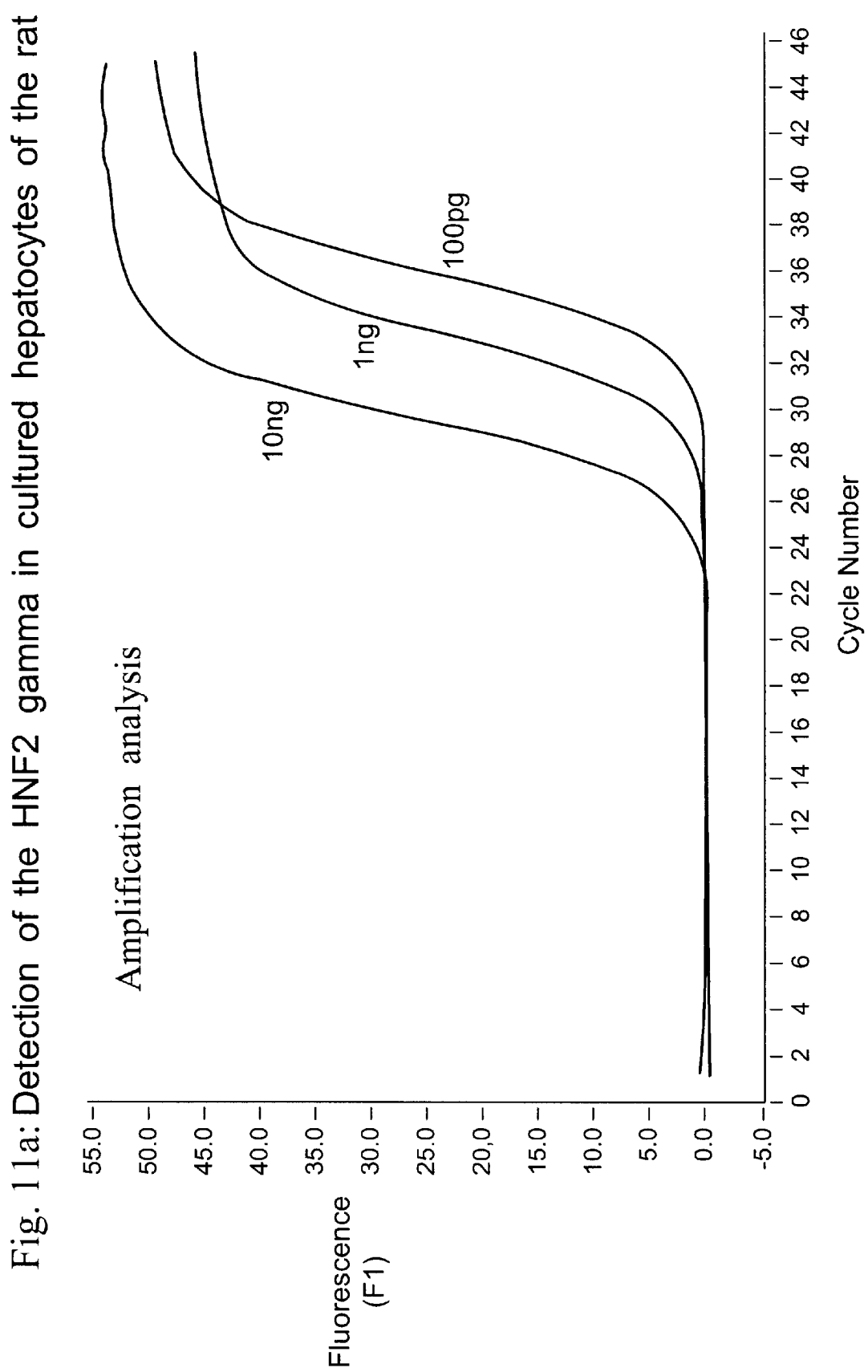

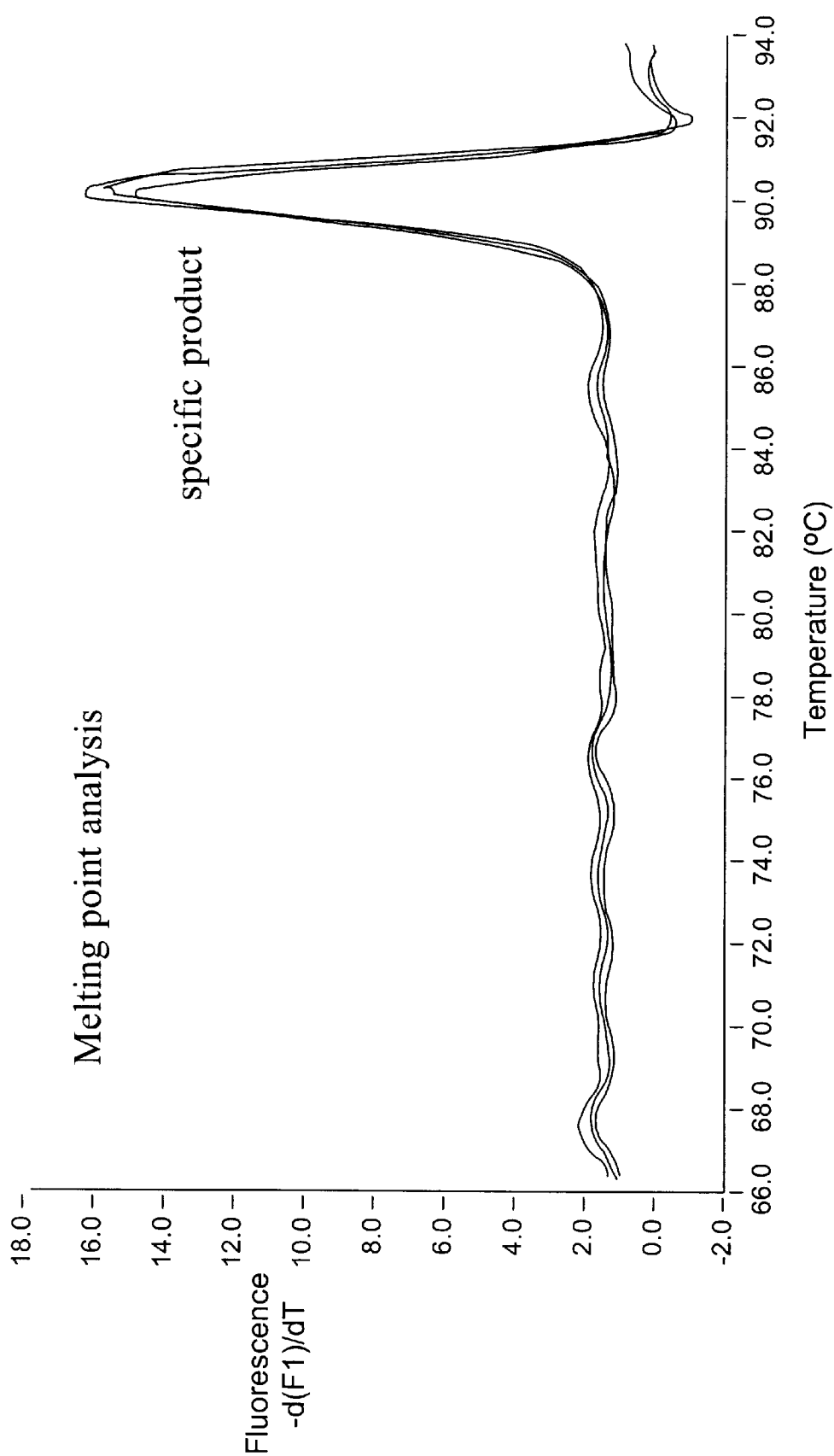
Fig. 11b: Detection of the HNF2 gamma in cultured hepatocytes of the rat

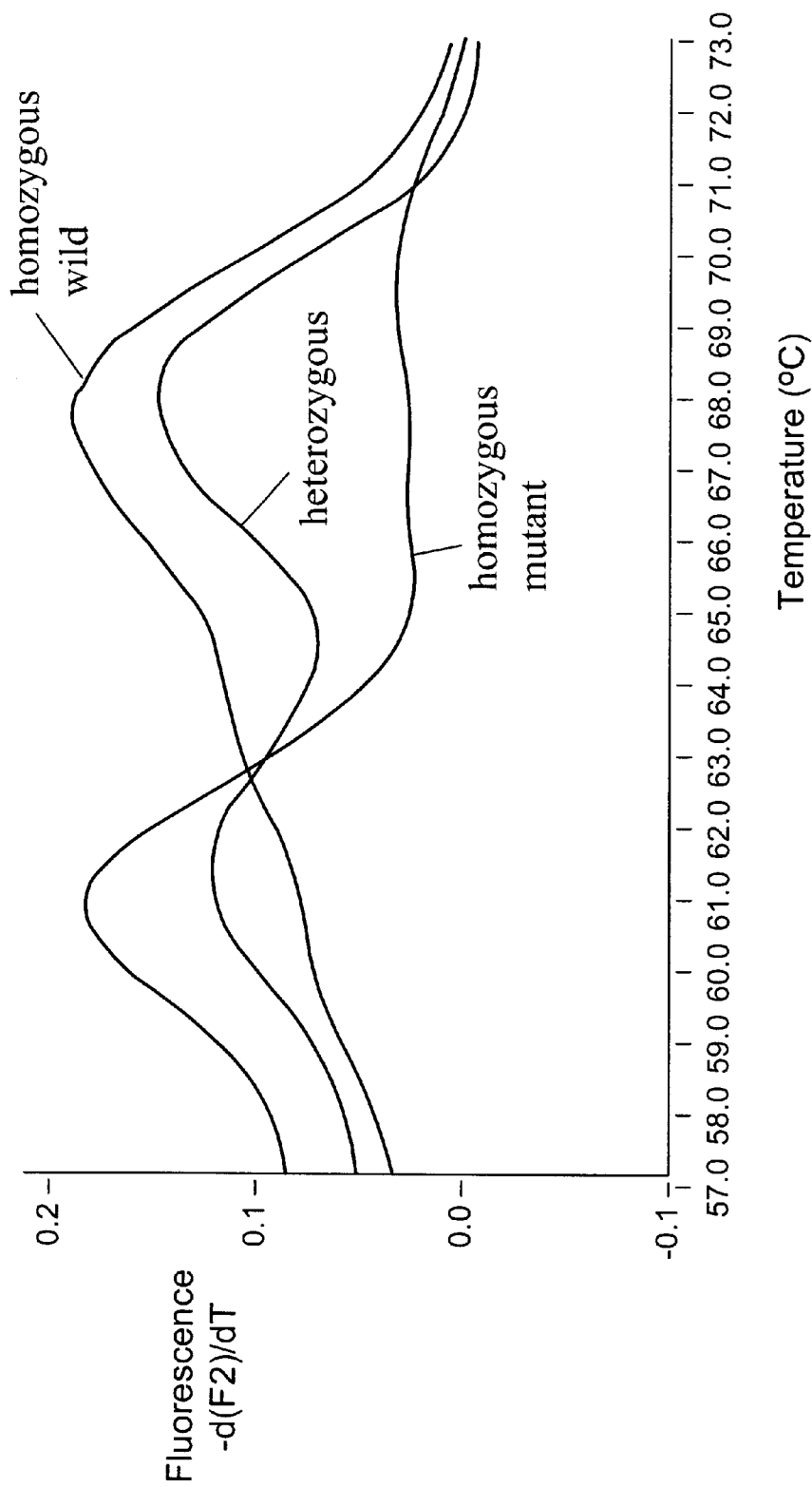
Fig. 12: Detection of the N-acetyl Transferase 2 Genotype in human DNA

PCR REACTION MIXTURE FOR FLUORESCENCE-BASED GENE EXPRESSION AND GENE MUTATION ANALYSES

BACKGROUND OF THE INVENTION

Gene expression occupies a key function in the evaluation of molecular processes in the body and great efforts are being made to investigate the significance of the expression of numerous genes also as a result of drug effects and to check it with respect to its predictive value in regard to the course of an illness and the success of a therapy.

A prerequisite for converting genetic information initially is the transcribing of the corresponding DNA sequence into mRNA. Gene expression can be regulated at the level of transcription as well as post-transcriptionally. For evidence-based medicine, the clarification of the mechanisms, which lead to a changed gene expression in the course of an illness, is an important objective, because new therapy concepts can be derived from it, which lead to an improved treatment of patients.

According to estimates of the organizers, the human genome project presumably will come to a conclusion in the year 2001. At the end of this project, which is being conducted worldwide, approximately 140,000 genes will have been identified. The analysis of the gene expression in different cell types and tissues, which provides important information concerning the normal state and the genesis of the pathologic state of cells and tissues, represents the greatest challenge at the present time as well as in the post-genome epoch.

A plurality of methods is employed for the analysis of gene expression, including Northern Blot and RT-PCR techniques. By means of chip-based technologies, that is, planar carriers of plastic, glass, gelatin, etc., on the surface of which a plurality of different (DNA) molecules, the positions of which are known and can be addressed, are disposed, thousands of genes can be investigated simultaneously with respect to their expression.

Aside from the different methods of analyzing gene expression, new technologies are being developed, in order to be able to detect nucleotide polymorphisms (that is, different variations of a gene) systematically, and to be able to evaluate them with respect to their biological significance in the course of an illness and, in the case of a medical application, in the sense of an individualized therapy.

A relatively recent method for fluorescence-based gene expression analyses and gene mutation analyses is represented by the investigation of amplified probes by the PCR technique in real-time PCR analytical equipment, such as the Lightcycler (Roche Diagnostics), TaqMan (Perkin-Elmer), etc.

The LightCycler is equipped with a three-channel fluorimeter, which can detect fluorescence at 530 nm (SYBR-Green), 640 nm (LC-RED 640) and 705 nm (LC-RED 7050). The manufacturer, Roche Diagnostics makes several tests available for the PCR amplification in the LightCycler, which can be used depending on the type of labeling (SYBR-Green or FRET methods; see below).

Dye Labeling

In order to be able to measure the newly synthesized in DNA in the subsequent real-time PCR, the DNA must be labeled by suitable dyes, which can be detected. For detecting the fluorescence signals, various real-time PCR detection systems were developed, with which it is possible to follow the whole of the PCR reaction. In the following, basic principles of the detection are explained:

1.) Fluorescence resonance energy transfer (FRET) is a process, for which a donor molecule, fluorescing after being stimulated by short-wave light, transfers its emission energy to a second acceptor molecule, which reacts to this with the emission of light of longer wavelength. The energy transfer from the one to the other molecule takes place over electron flow. The reporter molecule provides information concerning the product increase during the PCR. The so-called quencher molecule absorbs the fluorescence signals of the reporter molecule as long as both molecules are directly adjacent to one another in the hybridization probe. In this basic state, the reporter emission radiation for the fluorescence detector, with which the product increase in the PCR is measured, is invisible. Only as the PCR product increases, is there a spatial separation from the reporter and the quencher molecule. By these means, the reporter fluorescence becomes detectable and correlates directly with the amount of PCR product formed in the reaction.

A further method is referred to as the TaqMan method. In the case of the TaqMan method (or 5'-nuclease assay), the fluorescence-labeled hybridization probes bond to the complementary target strand between the primer binding sites. For the synthesis of the new strand, the hybridization probe is cut into small fragments by the 5'-3'-exonuclease activity of the Taq polymerases and released from the target strand. The reporter molecules and the quencher molecules are now present separately in the reaction mixture and the measured increase in the reporter fluorescence per PCR cycle correlates directly with the increase in the PCR product.

Other hybridization probes, synthesized according to the FRET principle, can be used for carrying out mutation analyses. Particularly important is the detection of so-called single nucleotide polymorphisms (SNPs), which come about due to the exchange of individual bases. Two hybridization probes, each labeled with a fluorescence dye, are used for the SNP analysis.

One donor probe binds directly adjacent to the mutation region. A second probe is produced so that it binds either complimentarily to the wild type or over the mutation site. In the melting point analysis, carried out after the PCR, the probe melts off at a particular temperature. If the probe bonds complimentarily to the wild type, it melts off at higher temperatures. On the other hand, in the presence of a mutation, the probe melts at lower temperatures. A mutation analysis therefore becomes possible. The fluorescence decline is calculated as a negative first derivative (as a melting peak). The mutation can be diagnosed by the displaced melting curve. This method with different fluorescence dyes can only be used by means of a real time detection system.

The principle of the real time detection system also forms the basis of the LightCycler from Roche Diagnostics. The LightCycler has three channels by means of which the emitted light quanta of dyes can be detected. DNA can by labeled with SYBR-Green; in addition, FRET probes, which are labeled with LC-Red 640 or LC-Red 705 dyes can also be used.

If the FRET method is used in the LightCycler, special hybridization probes must be added to the reaction mixture. They are labeled with fluorescein and LC red 640 or LC red 705 (from Roche Diagnostics). The fluorescence is observed only if both probes (donor probe and acceptor probe) have bonded in the immediate spatial vicinity to the target sequence. The transfer of light quanta (h*v), namely the fluorescence resonance energy transfer (FRET; see FIG. 1), then comes about.

2.) In the SYBR-Green method, the SYBR-Green intercalates in each case between two complementary base strands during the DNA synthesis and, with that, experiences a measurable increase in fluorescence as the PCR reaction progresses (see FIG. 2). However, the use of SYBR-Green lacks any specificity with regard to the template, which is to be investigated (that is, the DNA binding site), because the primer dimers, which are formed during the reaction, also cause an increase in fluorescence. Initially, this cannot be differentiated from the desired DNA synthesis product and can lead to wrong interpretations. However, it is possible to differentiate between the specific product and primer dimers at the end of the PCR by means of a melting curve analysis. For this, the PCR products are heated continuously over a particular temperature range and are present only as a single strand, depending on their melting point. The decrease in fluorescence, associated with this, is recorded. Smaller fragments, such as the primer dimers, have a melting point, which is lower than that of larger PCR products.

The representation of the fluorescence signal changes as a function of the temperature, derived from this, results in a curve, in which the specific PCR product becomes distinguishable from the primer dimers, if the melting points differ clearly from one another.

PCR Amplification in General

With the help of the polymerase chain reaction (PCR), clearly defined DNA sections of a gene can be reproduced million fold. For this purpose, two oligonucleotides (primers), which are complementary to the target sequence and each of which adds to one of the DNA strands, are added to the PCR reaction mixture. Moreover, sufficient amounts of the four desoxynucleoside triphosphates, a certain amount of magnesium chloride and a heat-stable DNA polymerase are added to the reaction cocktail. The individual substances for the PCR reaction are offered by numerous companies (Roche Diagnostics, Qiagen, Promega, Stratagene, TaKaRa, etc.). Previously prepared reaction mixtures or "Master-Mixes" are also offered, to which only the primers and the DNA, which is to be investigated, have to be pipetted.

However, because of the lower sensitivity and selectivity and due to the formation of primer dimers, which are false DNA synthesis products, the informative power of the fluorescence-based gene expression analyses and gene mutation analyses, using our own PCR reaction mixtures with the conventional components and concentrations or using the commercially obtainable MasterMixes, is very limited. The formation of primer dimers must be emphasized especially, since it can lead to false findings, as a result of which appreciable risks arise for the patient and for biomedical research in general and therefore a reliable medicinal diagnosis, for example, during accompanying investigations in the course of the therapy, cannot be guaranteed. Furthermore, these investigations are very cost intensive, especially when the Roche kits are used, as a result of which the number of possible investigations is greatly limited by the respective research budget.

SUMMARY OF THE INVENTION

It is therefore an object of the invention to increase the selectivity and sensitivity of fluorescence-based gene expression analyses and gene mutation analyses and, by suppressing the formation of primer dimers (see FIG. 3), to prevent wrong diagnoses and erroneous findings.

An increase in the selectivity, sensitivity and the suppression of primer dimer formations, fluorescence-based gene expression analyses and gene mutation analyses is accomplished pursuant to the invention owing to the fact that bovine serum albumin is added to the conventional PCR reaction components and that the magnesium chloride concentration is adjusted accurately depending on the Taq polymerase used. In SYBR-Green DNA labeling, the exact adjustment of the concentration is indispensable for realizing the inventive responses (sensitivity, selectivity).

The use of the inventive PCR reaction mixture leads to a clearly improved sensitivity and selectivity of fluorescence-based gene expression analyses and gene mutation analyses in the animal, bacterial, vegetable and human genome and prevents wrong diagnoses. By these means, it is possible to carry out such detections or investigations on samples, which previously could not be analyzed in this way because of their low RNA or DNA concentration. Moreover, the claimed invention leads to a dramatic reduction in the costs of the investigation.

The inventive PCR reaction mixture makes possible a distinct increase in the information power of the semiquantitative and totally quantitative determination of the gene expression in tissues and organs in the healthy, diseased and medicinally affected state. Moreover, because of the possibility of using inexpensive components in gene expression analyses or the detection of nucleotide polymorphisms, the use of the inventive PCR reaction mixture leads to a reduction in costs from about DM 4.13 per sample to DM 0.75 per sample.

The technical area of application of the invention comprises, above all, a) the pharmacogenomics and here, especially the discovery of genomic targets for drug candidates in research and development, or for products already introduced on the market, b) the detection of nucleotide polymorphisms, especially in the molecular diagnosis of diseases based on gene mutation analyses and gene polymorphism, in drug therapy and here, in particular, in the individualized dosing of drugs and for the rational interpretation of the pharmacokinetic course of a therapy, c) for the characterization of potential drugs at the gene expression level, d) the toxicogenomics and here, especially, the use in the case of toxicological investigations for preclinical development and for predicting toxic effects and for the toxicological characterization of individual materials and material mixtures at the gene expression level, e) the molecular diagnosis and here, especially the screening and the diagnosis of genes relevant to the illness, the monitoring of the course of an illness and a therapy and the molecular prognosis of diseases and f) the research and here, in particular, the identification of molecular interactions of materials, material mixtures and biological agents on the genome level, the identification of gene intercalations and the function analysis of new genes, including sequence analyses and gene clonings.

BRIEF DESCRIPTION OF THE DRAWINGS

FIG. 1—representation of the fluorescence resonance energy transfer (FRET) principal;

FIG. 2—representation of the SBYR-Green I labeling;

FIG. 3—melting curve analysis after amplification of the transcription factor HNF3α from cDNA cultured hepatocytes of the rat;

FIG. 4—detection of a gene polymorphism in Morbus Meulengracht patients;

FIG. 5—detection of the sarcoplasmatic calcium ATPase from cDNA obtained from the human heart, using the claimed method;

FIG. 6—detection of the beta-myosin heavy chain (MHC) gene from cDNA obtained from human heart tissue using the claimed method;

FIG. 7—detection of the brain natriuretic peptide (BNP) gene from cDNA obtained from human heart tissue;

FIG. 8—detection of the atrial natriuretic peptide (ANP) gene from cDNA of cultured cardiomyocytes of the rat, using the claimed method;

FIG. 9—detection of the alpha skeletal actin gene from cDNA of cultured cardiomyocytes of the rat, using the claimed invention;

FIG. 10—detection of the albumin gene from cDNA of cultured hepatocytes of the rat using the claimed method;

FIG. 11—detection of the transcription factor HNF-3gamma from the cDNA of cultured hepatocytes of the rat using the claimed method;

FIG. 12—detection of the N-acetyl transferase 2 allele 5*genotype of human lymphocytic DNA with FRET hybridization probes using the claimed method;

DESCRIPTION OF THE PREFERRED EMBODIMENTS

EXAMPLES

Obtaining Samples and Isolating Nucleic Acids

Figure 13A:
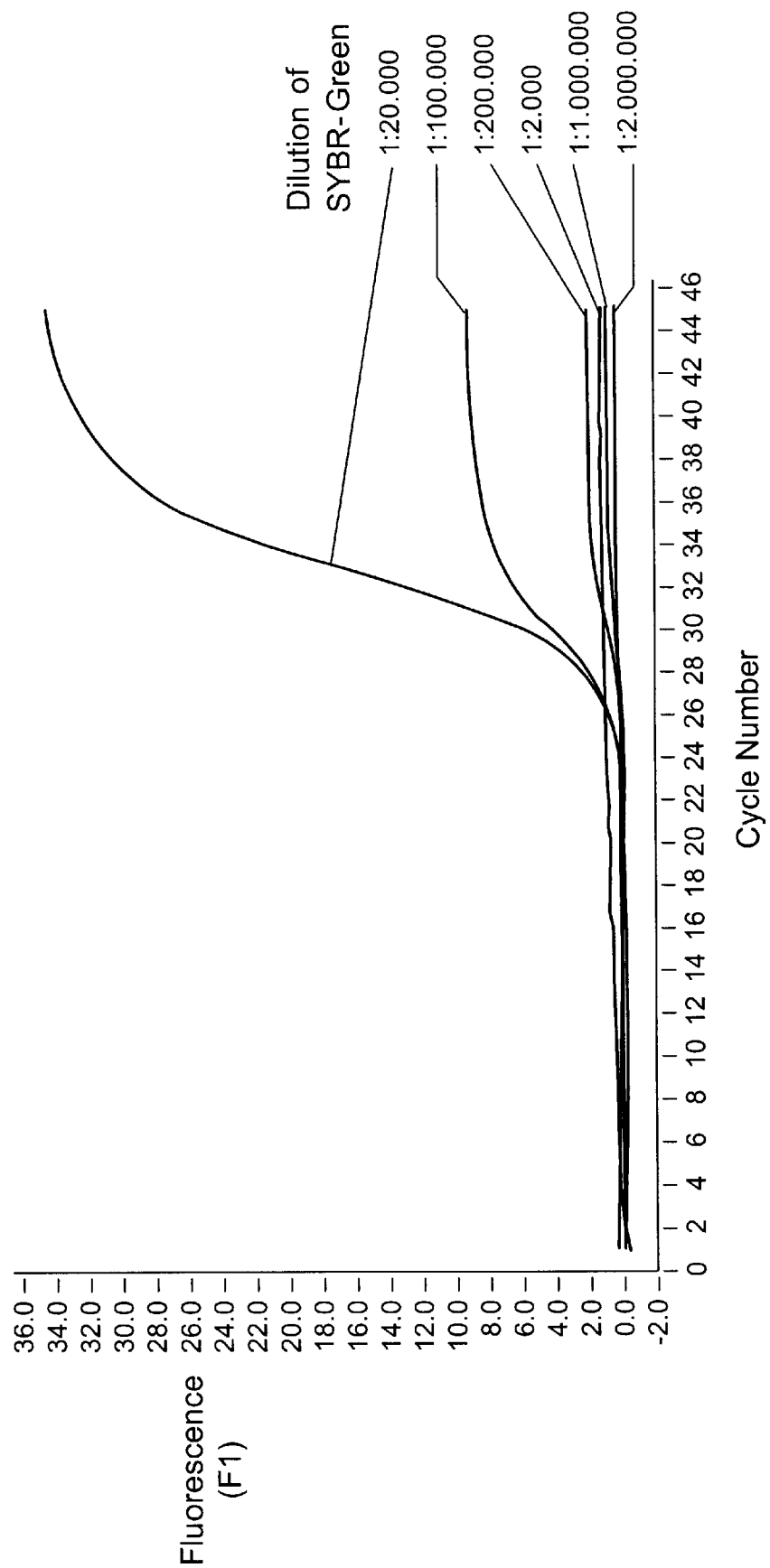
FIG. 13—representation of the concentration dependence of the SYBR-Green I labeling used in the claimed method.

To begin with, the biological material, which is to be investigated, is obtained in some suitable matter and isolated. After that, nucleic acids (RNA and DNA) are isolated from whole blood (nucleated lymphocytes) or animal/human tissue and purified. By means of standardized methods, DNA or RNA can be isolated from blood and/or tissue. When RNA is obtained, it must be transcribed into copyDNA before being used in the PCR, in order to be able to synthesize large amounts of the target DNA subsequently. For this purpose, a defined amount of RNA is transcribed into copyDNA by means of reverse transcriptase.

Example 1

Detection of a Gene Polymorphism in Morbus Meulengracht Patients

Morbus Meulengracht (Gilberts syndrome) is a disease, which is caused by a TA insertion polymorphism in the region of the TATA box of the uridine-5'-diphosphoglucose glucoronyl transferase gene (UGTIAI). Pursuant to the invention, a method was developed, in order to diagnose this polymorphism rapidly and simply.

After the blood samples are taken (200 µL of whole blood per patient, usually in EDTA-containing vessels, such as monovets), they are stored at −20° C. until the samples are worked up. The DNA of the nucleated blood cells is isolated by means of a DNA isolation kit and purified. The PCR reaction mixture (LightCycler DNA Master Hybridization Probes or LightCycler FastStartDNA Master Hybridization Probes (both Roche Diagnostics) or the inventive PCR reaction mixture (see Table 1)) is added to the cooled LightCycler capillary. For this purpose, specific oligonucleotide primers (each 400 nM), the hybridization probes (each 10 nM); donor probe labeled with fluorescein, acceptor probe with LC-RED 640) and the patient-specific DNA (2 µL) are pipetted to it.

The PCR reaction is then started with a 15-minute denaturing phase at 95° C. (In the case of the LightCycler DNA Master Hybridization Kit, the denaturing phase was 2 minutes). After that, the following cycle was repeated 50 times; 95° C. for 3 seconds, then 55° C. for 7 seconds and 72° C. for 12 seconds. After the PCR reaction, a melting point analysis is carried out. For this purpose, the synthesis products formed were heated to 45° C. and then slowly (0.2° C./second) to 80° C. During this period, the fluorescence is determined on-line in real time.

As soon as the hybridization probe, lying above the mutation that is to be detected, melts off, there no longer is any fluorescence resonance energy transfer (FRET, see above). The fluorescence is calculated using a special software by means of the graphically as the first negative derivative as a function of the temperature (−dF/dT vs T) (see FIG melting curves, which are then given. 4).

In the present example, the sensitivity of the inventive FRET reaction mixture is compared with that of Roche Diagnostics (LightCycler FastStart DNA Master Hybridization Probes). FIG. 4 shows that the inventive PCR mixture is up to 10,000 times more sensitive than the DNA Master Hybridization Probe Kit offered by Roche Diagnostics. Moreover, it is a decidedly important distinguishing feature that the melting curves are higher and narrower in the case of the claimed method; it is therefore possible to differentiate between the individual genotypes more specifically and more unambiguously with the inventive procedure than with the Roche Diagnostic Kit. This difference is of fundamental importance for the medical evaluation of neucleotide polymorphisms in medical diagnosis and for the individualized, dose-adapted therapy (see FIG. 4).

Example 2

Detection of Sarcoplasmatic Calcium ATPase from cDNA of the Human Heart by Means of SYBR-Green Labelings After an explantation of the human heart within the scope of a heart transplant, biopsy material was removed and frozen immediately in liquid nitrogen until it was processed further. Heart tissue (50 mg) was then removed and RNA was isolated and purified by standardized methods. RNA (2 µg) and random primer (Roche Diagnostics) are heated for 10 minutes at 70° C. in order subsequently to initiate the reverse transcription (60 minutes at 42° C.). Rnase inhibitor (40 U Stratagene), dNTPs (1 nM, Roche Diagnostics) and AMV reverse transcriptase (20 U, Promega) are pipetted into random primers and RNA buffer solution (Promega). The reaction is stopped by raising the temperature to 95° C. for 5 minutes.

Subsequently, the PCR reaction mixture (LightCycler DNA Master SYBR Green I or LightCycler FastStart DNA Master SYBR Green I (both Roche Diagnostics) or the PCR cocktail developed by us) is added to a LightCycler capillary. To this, 40 nM of the specific oligonucleotide primer and the corresponding copyDNA are pipetted.

At the end of a 15-minute denaturing phase at 95° C., the PCR reaction is started. (In the case of the LightCycler DNA Master SYBR Green I Kit, the denaturing phase was 2 minutes).

After that the following cycle is repeated 60 times: 95° C. for 3 seconds, then 55° C. for 7 seconds and 72° C. for 12 seconds. During each cycle, an actual fluorescence measurement was carried out at 87° C. in every capillary. From these measurements, the real time PCR curve shown in FIG. 5, was obtained. At the end of the PCR reaction, a melting point analysis is carried out. For this purpose, the DNA synthesis products are heated to 68° C. and then slowly (0.2° C./second) to 95° C. During this time period, the fluorescence is determined online. A specific melting temperature is reached for the respective DNA synthesis product. At this temperature, the added-on fluorescing SYBR Green molecules are detached from the melting DNA strands, as a result of which the fluorescence yield is decreased suddenly. The fluorescence behavior is converted by a special software into melting curves, which are then given graphically as the first negative derivative as a function of temperature (−dF/dT vs T) (see FIG. 5).

In this application example, the sensitivity of the claimed SYBR Green reaction mixture is compared with that of the Analysis Kit of Roche Diagnostics. FIG. 5 shows that the claimed method, in comparison to the Roche Diagnostics Kit, leads to a significantly improved, higher dynamics (fluorescence increase per-cycle) during the DNA synthesis. The dynamics (fluorescence loss per second) are also much higher for the melting point analysis, so that the melting point peaks are narrower and the amplitude higher, as a result of which the gene expression can be determined more specifically and therefore with greater accuracy.

In the following examples, the claimed reaction mixture was used successfully for the amplification of genes from human and animal tissues, which are relevant to diseases, and in cell culture experiments.

Example 3

Detection of Beta-Myosin-Heavy Chain (MHC) Gene from cDNA of the Human Heart by Means of SYBR Green Labelings After an explantation of the human heart within the scope of a heart transplant, biopsy material was removed and frozen immediately in liquid nitrogen until it was processed further. Heart tissue (50 mg) was then removed and RNA was isolated and purified by standardized methods. RNA (2 $\mu$g) and random primer (Roche Diagnostics) are heated for 10 minutes at 70° C. in order subsequently to initiate the reverse transcription (60 minutes at 42° C.). Rnase inhibitor (40 U Stratagene), dNTPs (1 nM, Roche Diagnostics) and AMV reverse transcriptase (20 U, Promega) are pipetted into random primers and RNA buffer solution (Promega).

Subsequently, the claimed PCR cocktail is added to a LightCycler capillary and 400 nM of the specific oligonucleo primer and the corresponding copyDNA were pipetted in (10 ng, 1 ng and 100 pg) are pipetted to it.

At the end of a 15-minute denaturing phase at 95° C., the PCR reaction is started. After that, the following cycle is repeated 38 times: 95° C. for 3 seconds, then 57° C. for 8 seconds and 72° C. for 12 seconds. During each cycle, an actual fluorescence measurement was carried out at 89° C. in every capillary. From these measurements, the real time PCR curve shown in FIG. 6, was obtained. At the end of the PCR reaction, a melting point analysis is carried out. For this purpose, the DNA synthesis products are heated to 68° C. and then slowly (0.2° C./second) to 95° C. During this time period, the fluorescence is determined online. A specific melting temperature is reached for the respective DNA synthesis product. At this temperature, the added-on fluorescing SYBR Green molecules are detached from the melting DNA strands, as a result of which the fluorescence yield is decreased suddenly. The fluorescence behavior is converted by a special software into melting curves, which are then given graphically as the first negative derivative as a function of temperature (−dF/dT vs T) (see FIG. 6).

Example 4

Detection of the Brain Natriuretic Peptide (BNP) Gene from cDNA of the Human Heart by Means of SYBR Green Labeling After an explantation of the human heart within the scope of a heart transplant, biopsy material was removed and frozen immediately in liquid nitrogen until it was processed further. Heart tissue (50 mg) was then removed and RNA was isolated and purified by standardized methods. RNA (2 $\mu$g) and random primer (Roche Diagnostics) are heated for 10 minutes at 70° C. in order subsequently to initiate the reverse transcription (60 minutes at 42° C.). Rnase inhibitor (40 U Stratagene) and AMV reverse transcriptase (20 U, Promega) are pipetted into random primers and RNA buffer solution (Promega). The reaction is stopped by raising the temperature to 95° C. for five minutes.

Subsequently, the claimed PCR cocktail is added to a LightCycler capillary and 400 nM of the specific oligonucleotide primer and the corresponding copyDNA are pipetted in (10 ng, 1 ng and 100 pg).

At the end of a 15-denaturing phase at 95° C., the PCR reaction is started. After that, the following cycle is repeated 46 times: 95° C. for 3 seconds, then 53° C. for 8 seconds and 72° C. for 10 seconds. During each cycle, an actual fluorescence measurement was carried out at 89° C. in every capillary. From these measurements, the real time PCR curve shown in FIG. 7, was obtained. At the end of the PCR reaction, a melting point analysis is carried out. For this purpose, the DNA synthesis products are heated to 68° C. and then slowly (0.2° C./second) to 95° C. During this time period, the fluorescence is determined online.

A specific melting temperature is reached for the respective DNA synthesis product. At this temperature, the added-on fluorescing SYBR Green molecules are detached from the melting DNA strands, as a result of which the fluorescence yield is decreased suddenly. The fluorescence behavior is converted by a special software into melting curves, which are then given graphically as the first negative derivative as a function of temperature (−dF/dT vs T) (see FIG. 7).

Example 5

Detection of the Atrial Natriuretic Peptide (ANP) Gene from cDNA of Cultured Cardiomyocetes of the Rat After the isolation and 48th culturing of adult cardiomyocetes of rats, the cells where harvested and immediately frozen in liquid nitrogen until they were processed further. The RNA was isolated and purified by means of standard methods. RNA (2 $\mu$g) and random primer (Roche Diagnostics) are heated for 10 minutes at 70° C., in order to initiate the reverse transcription subsequently (60 minutes at 42° C.). dNTPs (1 nM, Roche Diagnostics), Rnase inhibitor (40 U, Stratagene) to and AMV reverse transcriptase (as 20 U, Promega) were pipetted into random primers and RNA buffer solution (Promega). The reaction is stopped by raising the temperature to 95° C. for five minutes.

Subsequently, the claimed PCR cocktail is added to a LightCycler capillary. For this purpose, 400 nM of the specific oligonucleotide primer and the corresponding copyDNA is pipetted in (10 ng, 1 ng and 100 pg).

At the end of a 15-denaturing phase at 95° C., the PCR reaction is started. After that, the following cycle is repeated 55 times: 95° C. for 3 seconds, then 55° C. for 7 seconds and 72° C. for 12 seconds. During each cycle, an actual fluorescence measurement was carried out at 91° C. in every capillary. From these measurements, the real time PCR curve shown in FIG. 8, was obtained. At the end of the PCR reaction, a melting point analysis is carried out. For this purpose, the DNA synthesis products are heated to 68° C. and then slowly (0.2° C./second) to 95° C. During this time period, the fluorescence is determined online. A specific melting temperature is reached for the respective DNA synthesis product. At this temperature, the added-on fluorescing SYBR Green molecules are detached from the melting DNA strands, as a result of which the fluorescence yield is decreased suddenly. The fluorescence behavior is converted by a special software into melting curves, which are then given graphically as the first negative derivative as a function of temperature (−dF/dT vs T) (see FIG. 8).

Example 6

Detection of the Alpha Skeletal actin Gene from cDNA of Freshly Removed Heart Tissue of the Rat After an explantation of the rat heart, biopsy material was removed and frozen immediately in liquid nitrogen until it was processed further. RNA was isolated and purified by standardized methods. RNA (2 µg) and random primer (Roche Diagnostics) are heated for 10 minutes at 70° C. in order subsequently to initiate the reverse transcription (60 minutes at 42° C.). dNTPs (1 nM, Roche Diagnostics), Rnase inhibitor (40 U Stratagene) and AMV reverse transcriptase (20 U, Promega) are pipetted into random primers and RNA buffer solution (Promega). The reaction is stopped by heating to 95° C. for five minutes.

Subsequently, the claimed PCR cocktail is added to a LightCycler capillary and 400 nM of the specific oligonucleotide primer and the corresponding copyDNA are pipetted in (10 ng, 1 ng and 100 pg).

At the end of a 15-denaturing phase of 95° C., the PCR reaction is started. After that, the following cycle is repeated 46 of times: 95° C. for 3 seconds, then 55° C. for 7 seconds and 72° C. for 15 seconds. During each cycle, an actual fluorescence measurement was carried out at 90° C. in every capillary. From these measurements, the real time PCR curve shown in FIG. 9, was obtained. At the end of the PCR reaction, a melting point analysis is carried out. For this purpose, the DNA synthesis products are heated to 68° C. and then slowly (0.2° C./second) to 95° C. During this time period, the fluorescence is determined online. A specific melting temperature is reached for the respective DNA synthesis product. At this temperature, the added-on fluorescing SYBR Green molecules are detached from the melting DNA strands, as a result of which the fluorescence yield is decreased suddenly.

The fluorescence behavior is converted by a special software into melting curves, which are then given graphically as the first negative derivative as a function of temperature (−dF/dT vs T) (see FIG. 9).

Example 7

Detection of the Albumin Gene from cDNA of Cultured Hepatocytes of the Rat

After the isolation and culturing of hepatocytes of the rat for 48 hours, the cells where harvested and RNA was isolated and purified by means of standardized methods. RNA (2 µg) and random primer (Roche Diagnostics) are heated for 10 minutes at 70° C. in order subsequently to initiate the reverse transcription (60 minutes at 42° C.). dNTPs (1 nM, Roche Diagnostics), Rnase inhibitor (40 U Stratagene) and AMV reverse transcriptase (20 U, Promega) are pipetted into random primers and RNA buffer solution (Promega). The reaction is stopped by heating to 95° C. for five minutes.

Subsequently, the claimed PCR cocktail is added to a LightCycler capillary and 400 nM of the specific oligonucleotide primer and the corresponding copyDNA are pipetted in (10 ng, 1 ng and 100 pg).

At the end of a 15-denaturing phase of 95° C., the PCR reaction is started. After that, the following cycle is repeated 36 times: 95° C. for 3 seconds, then 55° C. for 7 and 72° C. for 12 seconds. During each cycle, an actual fluorescence measurement was carried out at 83° C. in every capillary. From these measurements, the real time PCR curve shown in FIG. 10, was obtained. At the end of the PCR reaction, a melting point analysis is carried out. For this purpose, the DNA synthesis products are heated to 68° C. and then slowly (0.2° C./second) to 95° C. During this time period, the fluorescence is determined online. A specific melting temperature is reached for the respective DNA synthesis product. At this temperature, the added-on fluorescing SYBR Green molecules are detached from the melting DNA strands, as a result of which the fluorescence yield is decreased suddenly. The fluorescence behavior is converted by a special software into melting curves, which are then given graphically as the first negative derivative as a function of temperature (−dF/dT vs T) (see FIG. 10).

Example 8

Detection of the Transcription Factor Hepatic Nuclear Factor (HNF) 3 Gamma from cDNA Cultured Hepatocytes of the Rat After the isolation and culturing of hepatocytes of the rat for 48 hours, the cells where harvested and RNA was isolated and purified by means of standardized methods. RNA (2 µg) and random primer (Roche Diagnostics) are heated for 10 minutes at 70° C. in order subsequently to initiate the reverse transcription (60 minutes at 42° C.). dNTPs (1 nM, Roche Diagnostics), Rnase inhibitor (40 U Stratagene) and AMV reverse transcriptase (20 U, Promega) are pipetted into random primers and RNA buffer solution (Promega). The reaction is stopped by heating to 95° C. for five minutes.

Subsequently, the claimed PCR cocktail is added to a LightCycler capillary and 400 nM of the specific oligonucleotide primer and the corresponding copyDNA are pipetted in (6 times 100 pg).

At the end of a 15-denaturing phase of 95° C., the PCR reaction is started. After that, the following cycle is repeated 46 times: 95° C. for 3 seconds, then 57° C. for 8 seconds and more will 72° C. for 12 seconds. During each cycle, an actual fluorescence measurement was carried out at 88° C. in every capillary. From these measurements, the real time PCR curve shown in FIG. 11, was obtained. At the end of the PCR reaction, a melting point analysis is carried out. For this purpose, the DNA synthesis products are heated to 66° C. and then slowly (0.2° C./second) to 95° C. During this time period, the fluorescence is determined online.

A specific melting temperature is reached for the respective DNA synthesis product. At this temperature, the added-on fluorescing SYBR Green molecules are detached from the melting DNA strands, as a result of which the fluorescence yield is decreased suddenly. The fluorescence behavior is converted by a special software into melting curves, which are then given graphically as the first negative derivative as a function of temperature (−dF/dT vs T) (see FIG. 11).

Example 9

Identification of the N-acetyl Transferase 2 Allele*Genotype from Human Lymphocytic DNA by Means of the FRET Method N-Acetyl transferase 2 is involved in the metabolization of many drugs. Patients with polymorphisms (gene mutations due to base exchange or deletions) have an increased-risk of being poisoned by side effects of drugs.

After blood samples are taken (200 µL of whole blood per patient usually in EDTA-containing vessels, such as monovettes), they are stored at −20° C. until they are worked up. The DNA is isolated from the nucleated blood cells and purified by means of a DNA isolation kit. The claimed PCR reaction mixture (see Table 1) is added to the cooled LightCycler capillary. For this purpose, specific oligonucleotides primers (400 nM of each), the hybridization probes (10 nM of each; donor probe labeled with fluorescein, acceptor probe with LC-RED 640) and the patient-specific DNA (2 µL) are pipetted in.

The PCR reaction is then started with a 15-minute denaturing phase at 95° C. (In the case of the LightCycler DNA Master Hybridization Kit, the denaturing phase lasted 2 minutes). After that, the following cycle was repeated 60 times: 95° C. for 3 seconds, then 45 ° C. for 10 seconds and 72° C. for 20 seconds. At the end of the PCR reaction, a melting point analysis is carried out. For this purpose, the synthesis products formed are heated to 45° C. and then slowly (0.2° C. per second) to 75° C. During this time period, the fluorescence is determined online. As soon as the hybridization probe, which lies above the mutations that is to be detected, melts off, there no longer is any fluorescence resonance energy transfer (see above). The fluorescence is calculated by means of the melting curves, using a special software. The melting curves are then given graphically as the first negative derivative as a function of temperature (−dF/dT vs T) (see FIG. 12).

Adjusting the Optimum PCR Reaction Mixture a) Adjusting the Optimum SYBR-Green Concentration SYBR-Green dilutions of 1:2,000 to 1:2,000,000 from the SYBR-Green stock solution were tested. The sarcoplasmatic calcium ATPase from cDNA, obtained from human heart, was amplified. The exact experimental conditions are described under Example 2. The largest measurable increase in fluorescence and, with that, the best result was achieved with a dilution of 1:20,000. As a result, the dynamics during the amplification and during the melting reached a maximum at a dilution of 1:20,000, so that, during the melting point analysis, the amplitude of the melting curves, produced by using an SYBR-Green dilutions of 1:20,000, are also the highest, as a result of which unambiguous findings are achieved. Other dilution steps, which are higher or lower than 1:20,000, produced results, which were distinctly inferior up to the point of the absence of detection (see FIG. 13).

b) Adjusting the Optimum MgCl$_2$ Concentration

Figure 13B:
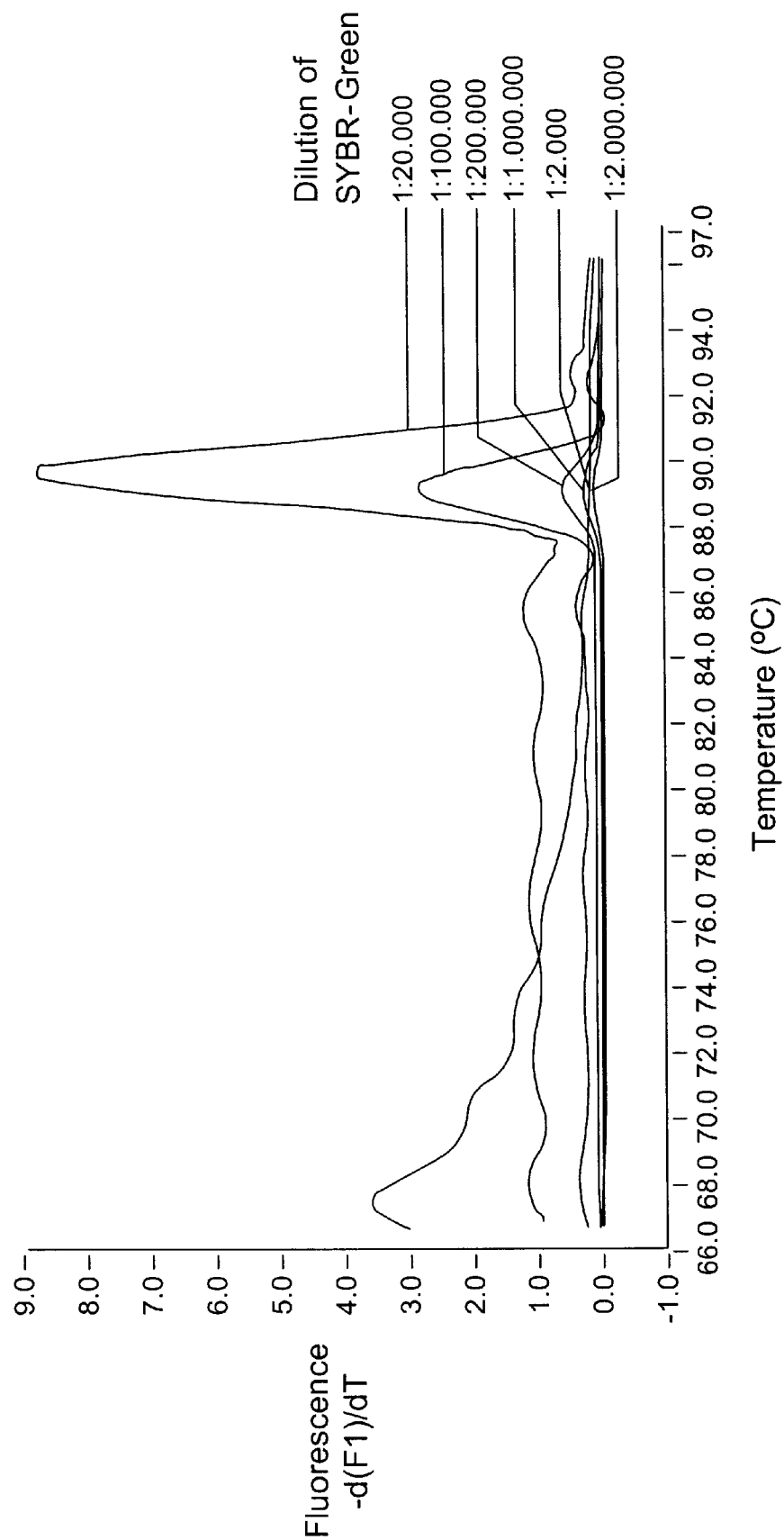

Increasing the MgCl$_2$ concentration from 1.5 mM over 3 mM to 5 mM led to a logical shortening of the start of the exponential (log) is DNA synthesis as is documented by the lower number of PCR cycles (see FIG. 13). An additional increase in the MgCl$_2$ concentration to 7 mM did not lead to any improvement in the analytics of the fluorescence increase.

Figure 14A:
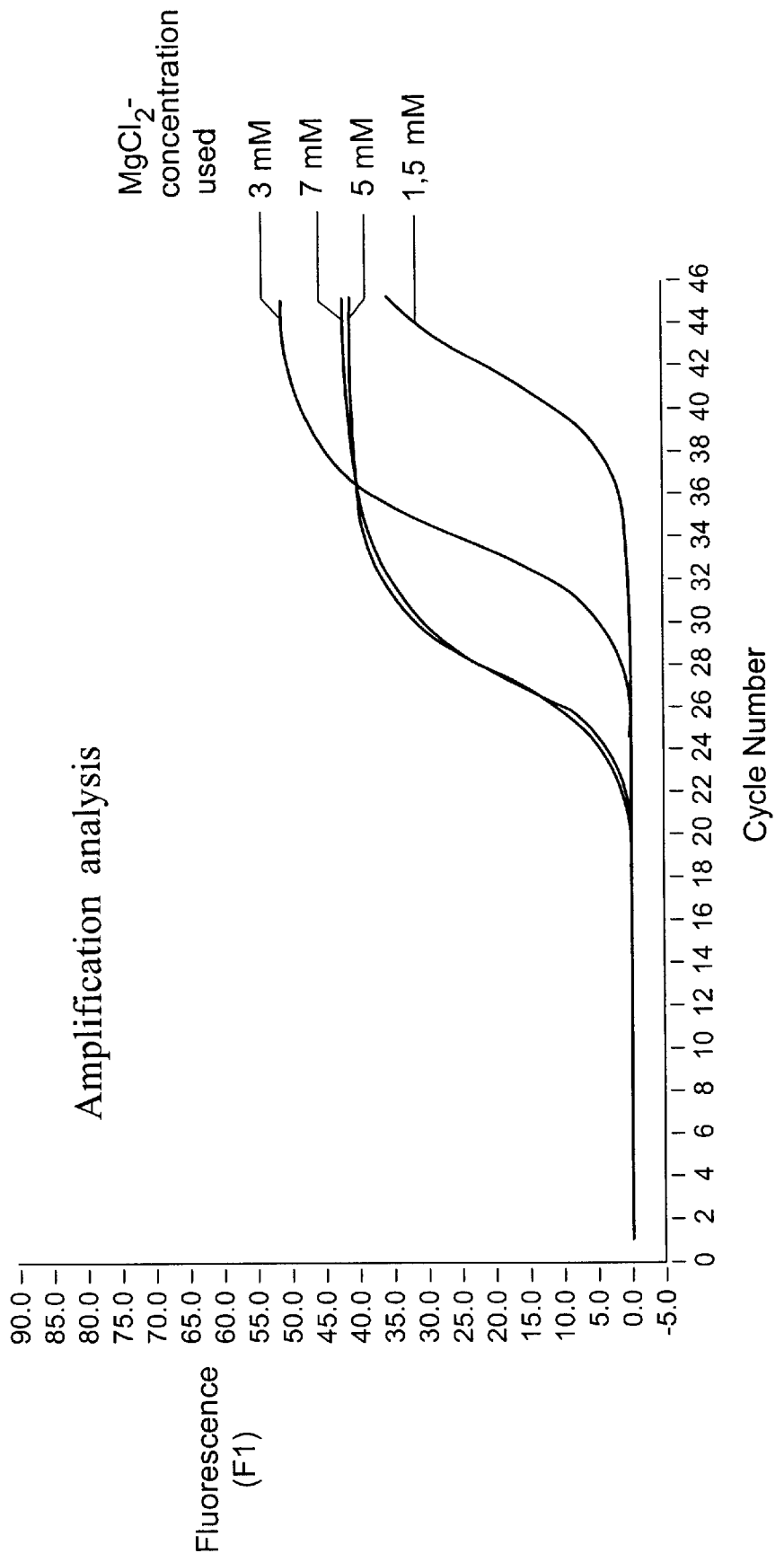
FIG. 14—representation of the concentration dependence of the $MgCl_2$ used in the claimed method.
Figure 14B:
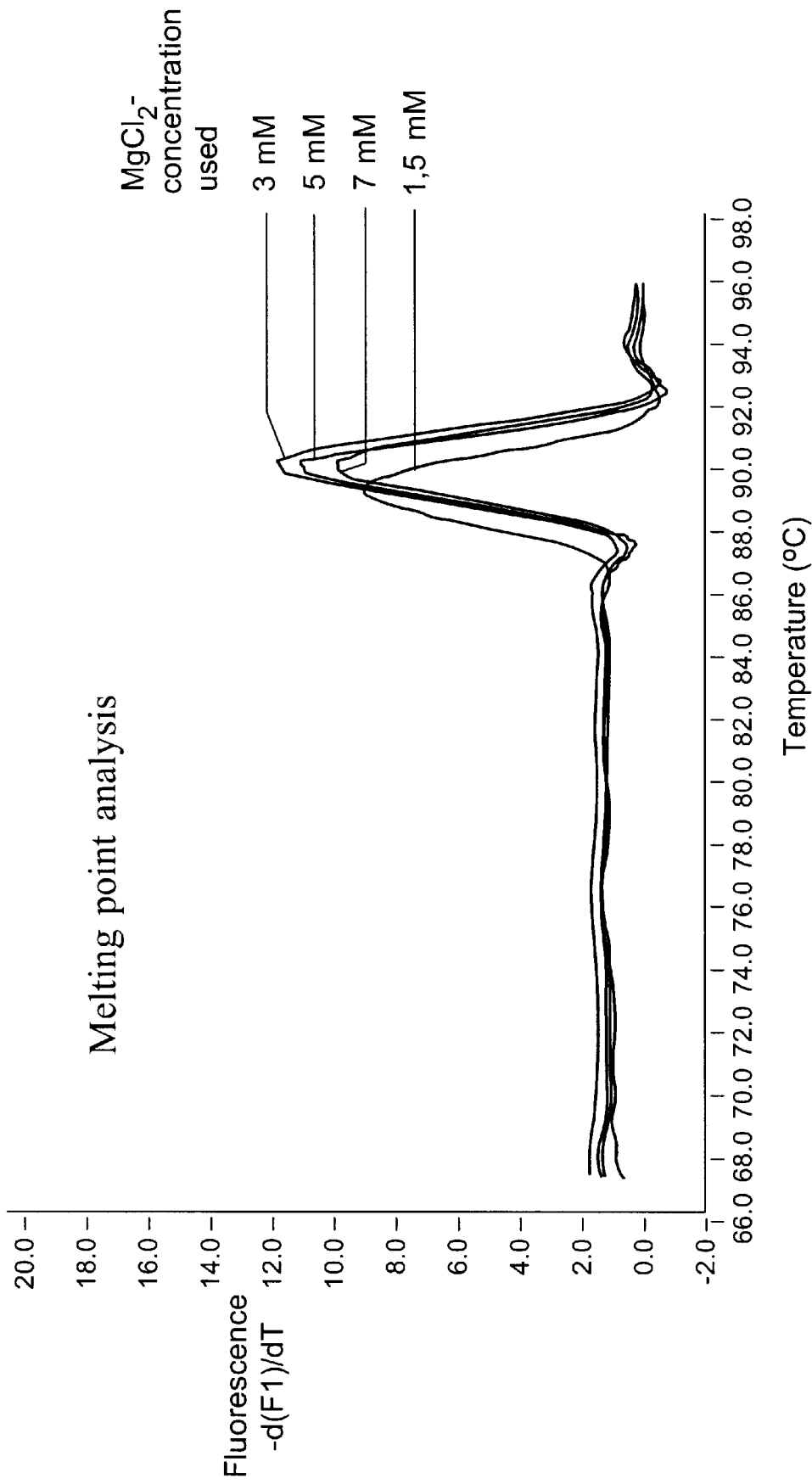

The amplitudes (heights) of the resulting melting curves are comparable for MgCl$_2$ concentrations of 3, 5 and 7 mM. The observed shift in the melting point curves to higher temperatures can be attributed to the different MgCl$_2$ concentration (see FIG. 14).

c) Adjustment of the Optimum BSA Concentration

Figure 15A:
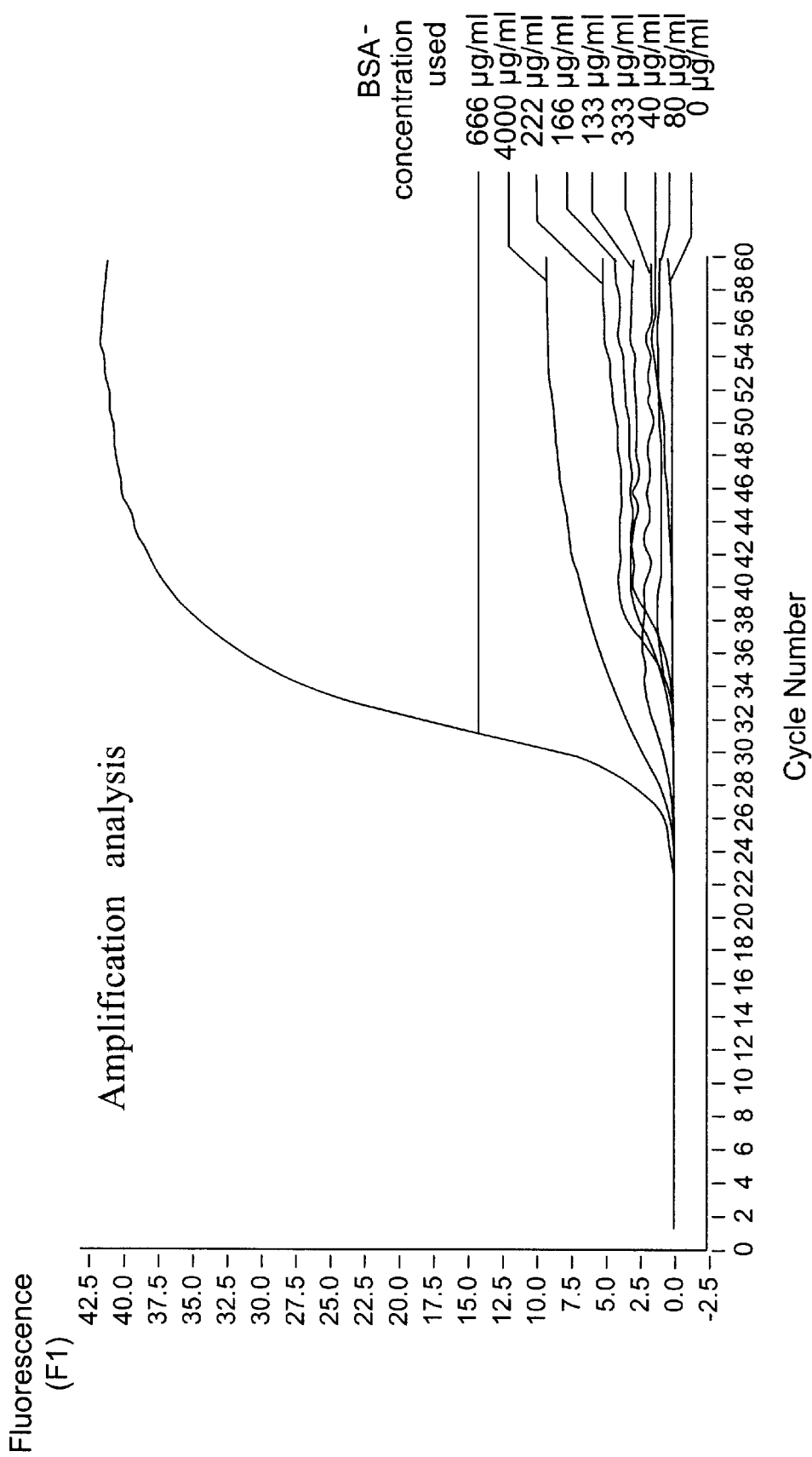
FIG. 15—representation of the concentration dependence of the BSA (bovine serum albumin) used in the claimed method.
Figure 15B:
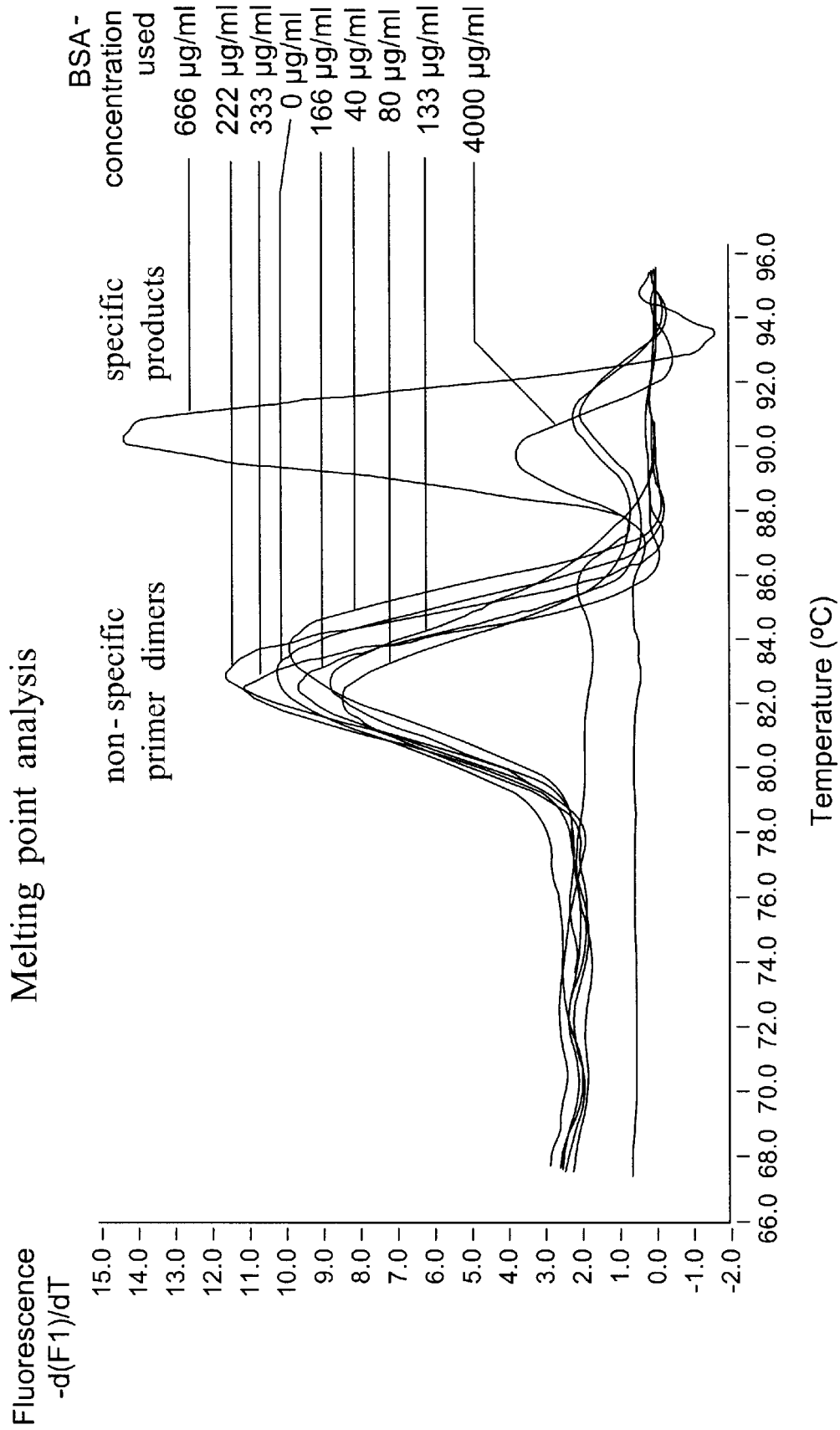

The best result was achieved at a concentration of 666 µg/mL of BSA. At this concentration, the dynamics of the fluorescence increase and of the melting off are the greatest. In contrast to the Roche Diagnostic Kit, non-specific primer dimers, which can lead to a faulty evaluation, are not formed in our claimed method at a BSA concentration of 666 µg/mL in the PCR reaction. If the BSA concentration is not adjusted accurately, there is pronounced primer dimer formation (see FIG. 15).

d) Dependence on the Taq Polymerase Used

Taq DNA polymerases from the different manufacturers (Taq DNA polymerase from Roche Diagnostics, Taq DNA polymerase from Life Technologies, PCR Supermix from Life Technologies, Platinum Taq polymerase from Life Technologies, Taq DNA Polymerase from Promega, Taq DNA polymerase from TaKaRa, Taq DNA polymerases from Qiagen, HotStart Taq DNA Polymerase Mastermix from Qiagen) were investigated. The best results way obtained with the HotStart Master Mix of Qiagen. Our claimed method can also be carried out with Taq polymerase is from other suppliers.

TABLE 1

Comparison of the composition of the claimed PCR reaction mixture using the HotStar TAQ polymerase Mastermixes with the commercially offered kit from Roche Diagnostics

| Roche Diagnostics | Claimed PCR Reaction Mixture |
|---|---|
| SYBR-Green Method | |
| 10 mM tris, pH 8.3 | HotStart TAQ polymerase |
| 50 mM KCl | Mastermix (Qiagen) 10 µL |
| 200 µM each of dATP. dCTP, dGTP | (2.5 U) |
| 400 µM dUTP | (tris-Cl, KCl, (NH$_4$)$_2$SO$_4$ pH 8.7 |
| 0.5 U TAQ DNA polymerase | HotStar Taq DNA polymerase |
| 2.5 mM MgCl$_2$ | MgCl$_2$ 3 mM |
| SYBR Green | dNTPs (200 µM) |
| The exact composition of the kit is not evident from cited patents of Roche Diagnostics (Patents EPO771870; U.S. Pat. No. 5,773,258; U.S. Pat. No. 5,677,152 | Bovine serum albumin (666 µg/mL) SYBR-Green I (dilution 1:20,000) MgCl$_2$ - added up to a final concentration of 5 mM. |
| FRET Method | |
| 10 mM tris, pH 8.3 | HotStart TAQ polymerase |
| 50 mM KCl | Mastermix (Qiagen) 10 µL |
| 200 µM each of dATP. dCTP, dGTP | (2.5 U) |
| 400 µM dUTP | (tris-Cl, KCl, (NH$_4$)$_2$SO$_4$ pH 8.7 |
| 0.5 U TAQ DNA polymerase | HotStar Taq DNA polymerase |
| 2.5 mM MgCl$_2$ | MgCl$_2$ 3 mM |
| | dNTPs (200 µM) The exact composition of the kit is not Bovine serum albumin evident from cited patents of Roche (666 µg/mL) Diagnostics (Patents EPO771870; MgCl$_2$ - added up to a final U.S. Pat. No. 5,773,258; U.S. Pat. No. concentration of 5 mM. 5,677,152 |

TABLE 2

Advantages of the Claimed Method/Disadvantages of the Roche Diagnostic Kit

| | Roche Diagnostics Kit | Thum/Borlak Method |
|---|---|---|
| Method FRET Method | sensitivity: detectable DNA/amount of cDNA LightCycler FastStart DNA Master Hybridization Probes 10 ng | sensitivity: detectable DNA/amount of cDNA claimed method: 10,000 times higher sensitivity than Roche method (1 pg of DNA) |
| | LightCycler DNA Master Hybridization Probe 10 pg | claimed method 10 times higher sensitivity (1 pg of DNA) |
| SYBR-Green Method | LightCycler DNA MasterSYBR Green 1: 1 pg | claimed method 7 times higher absolute fluorescence yield (1 pg) (see FIG. 4) |
| | LightCycler DNA Master SYBR Green 1 1 pg | claimed method 7 times higher absolute fluorescence yield (1 pg) |
| Primer - Dimer Formation | partially, pronounced primer - dimer formations, which can lead to faulty interpretations and findings | The primer - dimer formation is suppressed by the method claimed by us |
| Melting curve behavior | broad, low, (inaccurate) melting curve peaks, which can lead to faulty evaluations | Because of the improved melting behavior in the claimed method, a higher sensitivity can be achieved from the first negative derivative (−dF/dT) and, as can be seen from FIGS. 3 and 4, an accurate assignment of the DNA synthesis products in comparison to the Roche Diagnostics products. In comparison to the Roche Diagnostics products, the melting curve amplitude is up to 400% higher (see FIG. 4). |
| Dynamics of the amplification (in the log-linear phase) | Lower than in the case of the Thum/Borlak method (0.5 fluorescence units per PCR cycle) | In the claimed method, four times higher than in the case of the Roche Diagnostics Kit (2.0 fluorescence units per PCR cycle) (see FIG. 4) |
| Costs | | |
| SYBR-Green format | DM 3.75–4.13 per sample | DM 0.75 per sample |
| FRET format | DM 3.50–3.84 per sample | DM 0.75 per sample |

What is claimed is:

1. A PCR reaction mixture for fluorescence-based monitoring of a PCR reaction, comprising reaction components that further comprise at least one fluorescent component, a Taq DNA polymerase, $MgCl_2$, albumin, and wherein the at least one fluorescent component comprises a dye that participates in fluorescent energy transfer and/or intercalates into amplified DNA.

2. The PCR reaction mixture of claim 1, wherein the reaction mixture comprises bovine serum albumin.

3. The PCR reaction mixture of claim 1, wherein different Taq DNA polymerases are used.

4. The PCR reaction mixture of claim 1, wherein the $MgCl_2$ and the bovine serum albumin are added to commercially obtainable PCR reaction mixtures.

5. The PCR reaction mixture of claim 3, wherein the Taq DNA polymerase is a HotStart Polymerase Mastermix of QIAGEN.

6. The PCR reaction mixture of claim 5, wherein the $MgCl_2$ is added to the Mastermix up to a final concentration of about 5 mM.

7. The PCR reaction mixture of claim 1, wherein the bovine serum albumin is present in a final concentration of about 666 μg/mL.

8. The PCR reaction mixture of claim 4, wherein the $MgCl_2$ is adjusted to a total concentration of about 5 mM and bovine serum albumin is present in a final concentration of about 666 μg/mL.

9. The PCR reaction mixture of claim 2, wherein the SYBR-Green is used as a dye labeling.

10. The PCR reaction mixture of claim 9, wherein the SYBR-Green is added to the PCR reaction mixture.

11. The PCR reaction mixture of claim 10, wherein the SYBR-Green is diluted prior to adding to the mixture.

12. The PCR reaction mixture of claim 11, wherein the SYBR-Green is present in a dilution of 1:20,000.

13. The PCR reaction mixture of claim 2, wherein the at least one fluorescent component is capable of fluorescence resonance energy transfer.

14. The PCR reaction mixture of claim 2, wherein the at least one fluorescent components is capable of intercalating into amplified DNA.

15. The PCR reaction mixture of claim 1, wherein the reaction components comprise tris-Cl, KCl, $(NH_4)_2SO_4$, dNTPs, bovine serum albumin and either at least one fluorescent dye chosen from the group comprising SYBR-Green I, fluorescein and a fluorescent dye capable of fluorescence resonance energy transfer, and further comprising one or more oligonucleotides labeled with one of said fluorescent dyes.

16. The PCR reaction mixture of claim 3, wherein the Taq DNA polymerase is one that has been modified with at least one heat-labile blocking group so that the polymerase is inactive at ambient temperatures, and wherein incubating the polymerase at temperatures of 50° C. or more restores polymerase activity.

17. The PCR reaction mixture of claim 1, wherein the reaction mixture comprises at least one hybridizable probe, and wherein said probe is labeled with a fluorescent dye.

18. The PCR reaction mixture of claim 1, wherein the fluorescent dye is SYBR Green.

19. The PCR reaction mixture of claim 1, wherein the fluorescent dye is either LC-RED 640 or LC-RED 705.

20. The PCR reaction mixture of claim 1, wherein the albumin is present at a concentration of between 0.025 mg/ml and 1 mg/ml.

21. The PCR reaction mixture of claim 1, wherein the albumin concentration is between 0.5 mg/ml and 0.8 mg/ml.

22. The PCR reaction mixture of claim 17, wherein the hybridizable probe is conjugated to either SYBR Green or LC-RED 640 or LC-RED 705.

* * * * *